(12) United States Patent
Bulsara et al.

(10) Patent No.: US 10,869,825 B2
(45) Date of Patent: Dec. 22, 2020

(54) OCCLUSIVE FORMULATIONS

(71) Applicant: LG HOUSEHOLD & HEALTH CARE LTD., Seoul (KR)

(72) Inventors: Pallav Arvind Bulsara, Warren, NJ (US); Martyn J. Clarke, Zebulon, NC (US); Anthony V. Rawlings, Cheshire (GB)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 0 days.

(21) Appl. No.: 15/770,827

(22) PCT Filed: Oct. 25, 2016

(86) PCT No.: PCT/US2016/058585
§ 371 (c)(1),
(2) Date: Apr. 25, 2018

(87) PCT Pub. No.: WO2017/074896
PCT Pub. Date: May 4, 2017

(65) Prior Publication Data
US 2018/0303736 A1    Oct. 25, 2018

Related U.S. Application Data

(60) Provisional application No. 62/247,796, filed on Oct. 29, 2015.

(51) Int. Cl.
| | | |
|---|---|---|
| *A61K 8/06* | (2006.01) | |
| *A61K 8/34* | (2006.01) | |
| *A61K 8/55* | (2006.01) | |
| *A61Q 19/00* | (2006.01) | |
| *A61Q 19/08* | (2006.01) | |
| *A61K 8/81* | (2006.01) | |
| *A61K 8/36* | (2006.01) | |
| *A61K 8/02* | (2006.01) | |

(52) U.S. Cl.
CPC ............ *A61K 8/553* (2013.01); *A61K 8/0295* (2013.01); *A61K 8/062* (2013.01); *A61K 8/342* (2013.01); *A61K 8/345* (2013.01); *A61K 8/361* (2013.01); *A61K 8/8152* (2013.01); *A61Q 19/00* (2013.01); *A61Q 19/007* (2013.01); *A61Q 19/08* (2013.01)

(58) Field of Classification Search
CPC ... A61K 8/06; A61K 8/34; A61K 8/55; A61Q 19/00; A61Q 19/08
See application file for complete search history.

(56) References Cited

U.S. PATENT DOCUMENTS

| | | |
|---|---|---|
| 5,849,315 A | 12/1998 | Rerek et al. |
| 6,051,250 A | 4/2000 | Ribier et al. |
| 6,986,903 B2 | 1/2006 | Zulli et al. |
| 2006/0029657 A1 | 2/2006 | Popp et al. |
| 2010/0048740 A1 | 2/2010 | Mercier et al. |
| 2010/0189662 A1 | 7/2010 | Neubourg |
| 2012/0108661 A1 | 5/2012 | Orita et al. |
| 2013/0324499 A1 | 12/2013 | Pennick et al. |
| 2015/0147403 A1 | 5/2015 | Djedour |
| 2015/0272861 A1 | 10/2015 | Mazur et al. |

FOREIGN PATENT DOCUMENTS

| | | |
|---|---|---|
| CN | 103717196 A | 4/2014 |
| EP | 1 889 597 | 2/2008 |
| EP | 2 670 376 A2 | 12/2013 |
| EP | 2 926 833 | 10/2015 |
| FR | 3 010 306 | 3/2015 |
| WO | 98/19665 A1 | 5/1998 |
| WO | WO 98/19665 | 5/1998 |
| WO | WO 02/089770 A2 | 11/2002 |
| WO | WO 2013/007599 A2 | 1/2013 |
| WO | WO 2016/044374 A1 | 3/2016 |

OTHER PUBLICATIONS

"Emulmetik(TM), Biophilic(TM), 1-6,8,9, Amisol(TM) Soft Heliofeel(TM). Phospolipid-based emulsifiers" 14-18, Apr. 1, 2012 (Apr. 1, 2012), XP055116620, Retrieved from the Internet: URL:http://www.in-cosmetics.com/ novadocuments/10390; [retrieved on May 7, 2014; * pp. 3,6 *.
EP Search Report dated Jun. 3, 2019.
Summers et al The effect of lipids, with and without humectant, on skin xerosis, Soc 1-3 Costmet Chem., 1996, vol. 47, pp. 27-39 Entire Document.
U.S. Appl. No. 15/916,360.
U.S. Appl. No. 15/770,856.
U.S. Appl. No. 15/770,873.
G. Pennick, et al.: "The Effect of an Amphiphilic self-assembled lipid lamellar phase on the relief of dry skin", Int'l J of Cosmetic Science, 2012, 34; p. 567-574.
G. Pennick, et al., "Superior effect of isostearyl isostearate on improvement in stratum corneum water permeability barrier function as examined by the plastic occlusion stress test." Int J Cosmet Sci, 32 (2010)304-312.
Remco Hartkamp, et al.: "Composition Dependence of Water Permeation Across Multicomponent Gel-Phase Bilayers", J. Phys. Chem B. 2018, 122, 3113-3123.

(Continued)

*Primary Examiner* — Zohreh A Fay
(74) *Attorney, Agent, or Firm* — Vorys, Sater, Seymour & Pease LLP; Mih Suhn Koh

(57) ABSTRACT

The invention provides a topical o/w emulsion which moisturizes, and protects, repairs or restores the skin lipid barrier of a mammal. The topical o/w emulsion composition comprises a discontinuous oil phase; a continuous aqueous phase comprising water; a thickening agent; at least one lamellar membrane structure comprising a phospholipid, a fatty alcohol, and a fatty acid; and wherein in use the composition has a water vapor transmission rate of less than about 70 $g \cdot m^{-2} \cdot hr^{-1}$ measured in vitro using the modWVTR test methodology.

10 Claims, 2 Drawing Sheets

(56) References Cited

OTHER PUBLICATIONS

Daniël Groen et al., "Is an orthorhombic lateral packing and a proper lamellar organization important for the skin barrier function?" Biochimica et Biophysica Acta, (2011) 1529-1537.
Bianca Perez et al: "Ultralong Fatty Acyl Derivatives as Occlusive Structure Lipids for Cosmetic Applications: Synthesis and Characterization", ACS Sustainable Chemistry & Engineering, vol. 4, No. 12; Sep. 26, 2016 (Sep. 26, 2016), pp. 7137-7146, XP055589871, ISSN: 2168-0485, DOI: 10.1021/acssuschemeng.6b02021.
First Office Action for corresponding CN 201680076876.1, dated Jul. 2, 2020, with English translation.

OCCLUSIVE FORMULATIONS

This application is a 371 of International Application No. PCT/US2016/058585, filed Oct. 25, 2016, which claims the benefit of U.S. Provisional Application No. 62/247,796, filed Oct. 29, 2015, which is incorporated herein in its entirety.

FIELD OF THE INVENTION

The present invention relates to novel occlusive compositions for topical application.

BACKGROUND OF THE INVENTION

WO 2012/104604 describes a blend for use in personal care compositions, which comprises a dialkyl amphiphilic component and an ester of a branched fatty acid and a branched fatty alcohol. The blend may be used as the oil phase of an oil-in-water emulsion composition, and may further comprise a fatty acid and a fatty alcohol. Blends prepared in accordance with WO 2012/104604 are commercially available from Croda International PLC as DuraQuench™ blends. For example, DuraQuench™ IQ comprises potassium cetyl phosphate, isostearyl isostearate, behenic acid, cetyl alcohol and cetyl behenate. DuraQuench™ IQ SA comprises potassium cetyl phosphate, isostearyl isostearate, stearic acid, cetyl alcohol and cetyl stearate. The DuraQuench™ blends are adapted for use in personal care compositions and provide moisturization to the skin by forming a layer on the skin's surface and regulating water loss. See also Pennick et al., Intl J Cos Sci, 34, P 567-574 (2012).

U.S. Pat. No. 5,849,315 describes an emulsifier composition for skin care formulations that produces a bilayer lamellar gel network. The emulsifier composition comprises about 3-40% lecithin, and a blend of HLB emulsifier gellants comprising about 8-30% behenyl alcohol, about 15-30% glyceryl monostearate, about 15-40% of a mixture of palmitic and stearic acids, and 0-30% of maleated soybean oil. U.S. Pat. No. 5,849,315 also describes a skin care formulation containing about 2-7% of the emulsifier composition. Emulsifier compositions prepared in accordance with U.S. Pat. No. 5,849,315 are available from Ashland, Inc., and are marketed under the ProLipid® trade mark.

Stiefel Laboratories have marketed two topical o/w emulsion products for the foot and the hand, said products comprising Probiol Concentrate N03043S present in an amount of about 20%, and Behenyl Alcohol present in about 4-5% w/w ranges.

However, there remains a need in the art for cosmetically elegant compositions which have improved levels of occlusivity compared with those lipid mixtures described above, and in those products commercially sold.

Accordingly, an object of the present invention is to provide a topical composition that minimizes trans-epidermal water loss (TEWL), e.g. reduces the amount/quantity of water that passes from inside the body though the epidermal layer (skin) to the surrounding atmosphere.

A further object of the present invention is to provide a topical composition which is convenient, easily applied to the skin and cosmetically elegant.

SUMMARY OF THE INVENTION

One embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, and (ii) a fatty alcohol; and
wherein in use the composition has a water vapor transmission rate of less than about 70 $g \cdot m^2 \cdot hr'$ measured in vitro using the modWVTR test methodology.

Another embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, (ii) a fatty alcohol, and (iii) a fatty acid; and
wherein in use the composition has a water vapor transmission rate of less than about 70 $g \cdot m^2 \cdot hr'$ measured in vitro using the modWVTR test methodology.

Another embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, (ii) a fatty alcohol, (iii) a fatty acid, and (iv) an ester of a fatty alcohol and a fatty acid; and
wherein in use the composition has a water vapor transmission rate of less than about 70 $g \cdot m^2 \cdot hr'$ measured in vitro using the modWVTR test methodology.

Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, (ii) a fatty alcohol, and (iii) a fatty acid; and
wherein in use the composition has a water vapor transmission rate of less than about 70 $g \cdot m^2 \cdot hr^{-1}$ measured in vitro using the modWVTR test methodology.

Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, (ii) a fatty alcohol, (iii) a fatty acid, and (iv) an ester of a fatty acid and a fatty alcohol; and
wherein in use the composition has a water vapor transmission rate of less than about 70 $g \cdot m^2 \cdot hr'$ measured in vitro using the modWVTR test methodology.

Yet another embodiment of the disclosure is the use of a topical oil-in-water emulsion composition comprising:
(a) a discontinuous oil phase;
(b) a continuous aqueous phase comprising water;
(c) a thickening agent;
(d) at least one lamellar membrane structure comprising
    (i) a phospholipid, (ii) a fatty alcohol, and (iii) a fatty acid; and wherein in use the composition has a water vapor transmission rate of less than about 70 g·m$^{-2}$·hr$^{-1}$ measured in vitro using the modWVTR test methodology, for moisturizing, and protecting, repairing, or restoring the skin lipid barrier of a mammal.

One embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, and (iii) a fatty acid ester; and wherein in use the composition has a water vapor transmission rate of less than about 70 g·m$^2$·hr$^{-1}$ measured in vitro using the modWVTR test methodology A further embodiment of the disclosure is a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, (iii) a fatty acid, and (iv) a fatty acid ester; and
wherein in use the composition has a water vapor transmission rate of less than about 70 g·m$^{-2}$·hr$^{-1}$ measured in vitro using the modWVTR test methodology, for use in moisturizing, and protecting, repairing, or restoring the skin lipid barrier of a mammal.

Yet a further embodiment of the disclosure is the use of a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, (iii) a fatty acid, and (iv) a fatty acid ester; and
wherein in use the composition has a water vapor transmission rate of less than about 70 g·m$^{-2}$·hr$^{-1}$ measured in vitro using the modWVTR test methodology, in the manufacture of a cosmetic or pharmaceutical composition for moisturizing, and protecting, repairing, or restoring the skin lipid barrier of a mammal.

DETAILED DESCRIPTION OF THE INVENTION

Figure 1:
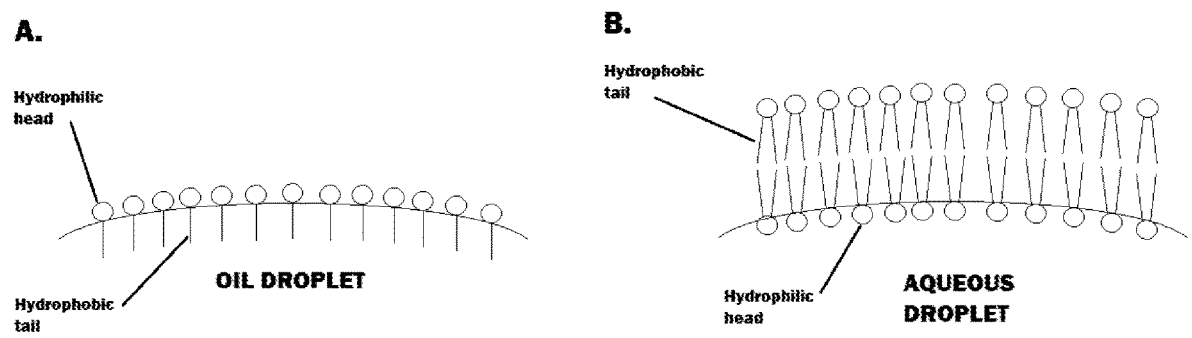
FIG. 1 illustrates key physical differences between an oil in water emulsion that can form a lamellar structure (A) and a liposome (B).
Figure 2:
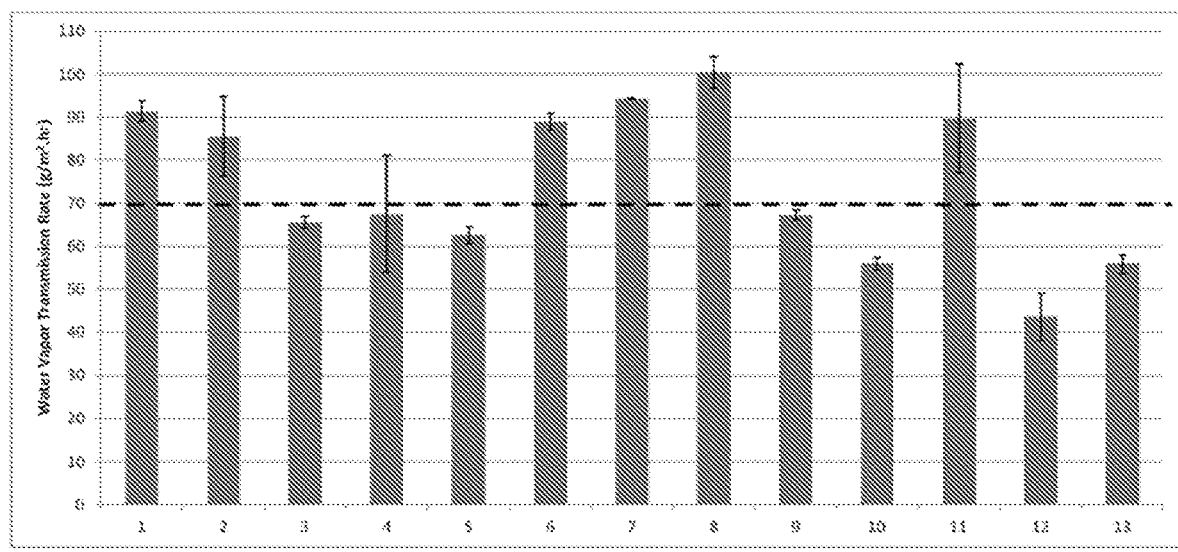
FIG. 2 illustrates the water vapor transmission rate (WVTR) for Formulations 1-13.

In one embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, and (ii) a fatty alcohol; and
wherein in use the composition has a water vapor transmission rate of less than about 70 gm$^{-2}$·hr$^{-1}$ measured in vitro using the modWVTR test methodology.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, and (iii) a fatty acid; and
wherein in use the composition has a water vapor transmission rate of less than about 70 gm$^{-2}$·hr$^{-1}$ measured in vitro using the modWVTR test methodology.

The emulsion compositions of the present invention have improved levels of occlusivity compared with prior art compositions.

In one embodiment, the composition is a cream, lotion, balm, lip cream or stick lip balm. In an embodiment, the composition is a cream. In another embodiment, the composition is a lotion. In a further embodiment, the composition is a balm. In yet a further embodiment, the composition is a lip cream. In another embodiment, the composition is a stick lip balm.

According to the invention, the topical composition in use has a water vapor transmission rate (WVTR) of less than about 70 g·m$^{-2}$·hr$^{-1}$ measured in vitro using the modWVTR test methodology. In an embodiment, the composition in use has a water vapor transmission rate of less than about 65 g·m$^{-2}$·hr$^{-1}$ measured in vitro using the modWVTR test methodology. In one embodiment, the composition in use has a water vapor transmission rate of less than about 62 g·m$^{-2}$·hr$^{-1}$ measured in vitro using the modWVTR test methodology. In another embodiment, the composition in use has a water vapor transmission rate of less than about 60 g·m$^{-2}$·hr$^{-1}$ measured in vitro using the modWVTR test methodology. In yet another embodiment, the composition in use has a water vapor transmission rate of less than about 50 g·m$^{-2}$·hr$^{-1}$ measured in vitro using the modWVTR test methodology.

In one embodiment, the composition in use has a water vapor transmission rate from about 35 g·m$^{-2}$·hr$^{-1}$ to about 70 g·m$^{-2}$·hr$^{-1}$ measured in vitro using the modWVTR test methodology. In a further embodiment, the composition in use has a water vapor transmission rate from about 40 g·m$^{-2}$·hr$^{-1}$ to about 70 g·m$^{-2}$·hr$^{-1}$ measured in vitro using the modWVTR test methodology. In yet a further embodiment, the composition in use has a water vapor transmission rate from about 40 g·m$^{-2}$·hr$^{-1}$ to about 65 g·m$^{-2}$·hr$^{-1}$ measured in vitro using the modWVTR test methodology. In an embodiment, the composition in use has a water vapor transmission rate from about 40 g·m$^{-2}$·hr$^{-1}$ to about 60 g·m$^{-2}$·hr$^{-1}$ measured in vitro using the modWVTR test methodology.

In an embodiment, the composition in use has a water vapor transmission rate of about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 or 70 g·m$^{-2}$·hr$^{-1}$ measured in vitro using the modWVTR test methodology.

Oil Phase

The compositions of this disclosure comprise a discontinuous oil phase. The discontinuous oil phase is dispersed throughout the continuous aqueous phase.

In an embodiment, the discontinuous oil phase comprises at least one oil and/or fat. For purposes herein oil, lipid and fat are used interchangeably. In one embodiment, the oil and/or fat is a mixture of two or more oils and/or fats.

Exemplary oils and fats include, but are not limited to, fatty acids, a source of fatty acids, fatty alcohols, esters, esters of glycerin (including mono-, di- and tri-esters), waxes, sterols, hydrocarbons, essential oils, vegetable oils and edible oils, and mixtures thereof.

In an embodiment, the at least one oil and/or fat is a fatty acid which may be saturated or unsaturated, branched or straight chain. Exemplary fatty acids include, but are not limited to, lauric acid, tridecylic acid, myristic acid, pentadecylic acid, palmitic acid, margaric acid, stearic acid, isostearic acid, oleic acid, linoleic acid, linolenic acid, ricinoleic acid, columbinic acid, nonadecylic acid, arachidic acid, arachidonic acid, eicosapentanoic acid, heneicosylic acid, behenic acid, tricosylic acid, lignoceric acid, nervonic acid, pentacosylic acid, cerotic acid, heptacosylic acid, montanic acid, nonacosylic acid, melissic acid, henatriacontylic acid, lacceroic acid, psyllic acid, geddic acid, ceroplastic acid and hexatriacontylic acid, and mixtures thereof.

The fatty acid can be introduced into the present compositions from a variety of sources. In an embodiment, the fatty acid is provided in the composition as an oil or wax. Examples of oils or waxes useful in this regard include, but are not limited to, rice bran oil, rice bran wax, flaxseed oil, hempseed oil, pumpkin seed oil, canola oil, soybean oil, wheat germ oil, olive oil, grapeseed oil, borage oil, evening primrose oil, black currant seed oil, chestnut oil, corn oil, safflower oil, sunflower oil, sunflower seed oil, cottonseed oil, peanut oil, sesame oil and olus (vegetable) oil, including hydrogenated and non-hydrogenated versions thereof, and mixtures thereof An exemplary wax useful in this regard is rice bran wax.

In one embodiment, the source of fatty acids is shea butter, also known as Butyrospermum parkii, if chemically treated. Shea butter comprises five principal fatty acids, namely palmitic acid, stearic acid, oleic acid, linoleic acid and arachidic acid. Shea butter also comprises phytosterols.

In another embodiment, the at least one oil and/or fat is a fatty alcohol which may be saturated or unsaturated, branched or straight chain. In one embodiment, the fatty alcohol is suitably a $C_{12}$-$C_{36}$ branched or straight chain fatty alcohol. In one embodiment, the $C_{12}$-$C_{36}$ chain is branched. In another embodiment the component is a $C_{14}$-$C_{26}$ branched or straight chain fatty alcohol. In one embodiment, the $C_{14}$-$C_{26}$ chain is branched. In another embodiment it is a $C_{16}$ to $C_{22}$ branched or straight chain fatty alcohol. In one embodiment, the $C_{16}$ to $C_{22}$ chain is branched. In another embodiment, the fatty alcohol is a branched or straight chain $C_{20}$-$C_{26}$ fatty alcohol. In one embodiment, the $C_{20}$-$C_{26}$ chain is branched. In yet another embodiment the fatty alcohol is a $C_{18}$ or $C_{22}$ or $C_{24}$ branched or straight chain fatty alcohol. In one embodiment, the Cis or $C_{22}$ or $C_{24}$ fatty alcohol chain is branched.

Exemplary fatty alcohols include, but are not limited to, decyl alcohol, lauryl alcohol, tridecyl alcohol, myristyl alcohol, pentadecyl alcohol, cetyl alcohol, isocetyl alcohol, cetearyl alcohol, palmitoleyl alcohol, heptadecyl alcohol, stearyl alcohol, isostearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, lanolin alcohol and palm alcohol, and mixtures thereof. In one embodiment, the fatty alcohol is behenyl alcohol, cetyl alcohol, stearyl alcohol or mixtures thereof. In one embodiment, the fatty alcohol is behenyl alcohol. In another embodiment, the fatty alcohol is cetyl alcohol.

In yet another embodiment, the at least one oil and/or fat is an ester. Exemplary esters include, but are not limited to, coco-caprylate/caprate, diethyl sebacate, diisopropyl adipate, diisopropyl dilinoleate, ethyl oleate, ethylhexyl hydroxystearate, glycol distearate, glycol stearate, hydroxyoctacontanyl hydroxystearate, isopropyl isostearate, isostearyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG-20 methyl glucose ether distearate, propylene glycol diacetate, propylene glycol dicaprylate, propylene glycol monolaurate, propylene glycol monopalmitostearate, propylene glycol ricinoleate and sucrose distearate, and mixtures thereof.

In another embodiment, the ester is isostearyl isostearate.

In another embodiment, the ester is other than cetyl lactate.

In a further embodiment, the at least one oil and/or fat is an ester of glycerin (including mono-, di- and tri-esters). Exemplary esters of glycerin include, but are not limited to, caprylic/capric triglycerides, caprylic/capric/succinic triglyceride, cocoglycerides, glyceryl citrate, glyceryl isostearate, glyceryl laurate, glyceryl monostearate, glyceryl oleate, glyceryl palmitate, glyceryl ricinoleate, glyceryl stearate, mono and diglyceride, PEG-12 glyceryl laurate, PEG-120 glyceryl stearate, polyglyceryl-3 oleate, polyoxyl glyceryl stearate, tallow glycerides and medium chain triglycerides, and mixtures thereof. In one embodiment, the ester of glycerin is caprylic/capric triglyceride.

In one embodiment, the ester of glycerin is other than glyceryl monosterarate. In another embodiment if the ester of glycerin is glyceryl monosterarate than the oil phase comprises a second oil or fat. In another embodiment, if the ester of glycerin is glyceryl monostearate than the oil phase comprises a second and different ester of glycerine.

In yet a further embodiment, the at least one oil and/or fat is a wax. Exemplary waxes include, but are not limited to, animal waxes, plant waxes, mineral waxes, silicone waxes, synthetic waxes and petroleum waxes. Suitable waxes include, but are not limited to, rice bran wax, carnauba wax, paraffin wax, white wax, candelilla wax, beeswax, jojoba wax, ozokerite and a spingolipid or a spingolipid mimic such as a ceramide, and mixtures thereof. In one embodiment the waxes are rice bran wax, carnauba wax, paraffin wax, white wax, candelilla wax, beeswax, jojoba wax and ozokerite, and mixtures thereof.

In an embodiment, the at least one oil and/or fat is wax is a sphingolipid or a sphingolipid mimic. Ceramides, acylceramides and glucosylceramides are all members of the "sphingoid" or "spingolipids" class. As noted above, these are compounds which have a backbone of sphingosine or a closely related structure to which either fatty acids or ω-esterified fatty acids are linked through an amide linkage at the amino group of the sphingosine structure and in the case of a glucosylceramide, those to which saccharide moieties are linked to the terminal hydroxyl of the sphingosine structure through a glycosidic bond.

More specifically, ceramides are a family of lipid molecules composed of sphingosine and a fatty acid. They contain an acyl linkage, and most abundant chain length in healthy skin is $C_{24}$-$C_{26}$ with a small fraction having an acyl chain length of $C_{16}$-$C_{18}$. Ceramides are found extensively in the stratum corneum. Ceramides are commercially available from major chemical suppliers such as Evonik, Mobile, Ala., USA or Sigma Chemical Company, St. Louis, Mo., U.S.A.

Exemplary ceramides useful in the present compositions include, but are not limited to, ceramide-1, -2, -3, -4, -5, -6 or -7, and mixtures thereof. Other ceramides known to those of skill in the art as useful in topical compositions are further contemplated as useful in the present compositions. In one embodiment, the ceramide is ceramide-3. Suitably, the ceramide if present is in the lamellar membrane structure in an amount from about 0.001% to about 1% by weight, based on the total weight of the composition.

In one embodiment, the sphingoid or sphingolipid is a ceramide or a phytospingosine. In one embodiment, the sphingoid or sphingolipid is a phytospingosine.

In an embodiment, the at least one oil and/or fat is a sterol. Exemplary sterols include, but are not limited to, *Brassica Campestris* sterols, $C_{10}$-$C_{30}$ cholesterol/lanosterol esters, canola sterols, cholesterol, *glycine soja* sterols, PEG-20 phytosterol and phytosterols, and mixtures thereof. In one embodiment, the sterol is a phytosterol.

Phytosterols are natural components of common vegetable oils. Exemplary sources of phytosterols useful in this regard include, but are not limited to, shea butter, vegetable oil, tall oil, sesame oil, sunflower oil, sunflower seed oil, rice bran oil, cranberry seed oil, pumpkin seed oil and avocado wax, and mixtures thereof. In one embodiment, the source of phytosterols is shea butter.

Phytosterols are typically incorporated in the basal membrane of the skin and can pass to the skin's surface through the differentiation of skin cells. Accordingly, phytosterols provide an improved caring and protecting effect. The topical application of phytosterols also usually leads to an increased skin moisture level and to increased lipid content. This improves the desquamation behavior of the skin and reduces erythemas which may be present. R. Wachter, Parf. Kosm., Vol. 75, p. 755 (1994) and R. Wachter, Cosm. Toil., Vol. 110, p. 72 (1995), each of which are incorporated herein by reference in their entirety, further demonstrate these advantageous properties of phytosterols.

Suitably, the phytosterol, source of phytosterols, cholesterol, or cholesterol derivative is present in the at least one lamellar membrane structure in an amount from about 0.05% to about 2% by weight, based on the total weight of the composition.

One embodiment of the composition is the inclusion of a phytosterol, cholesterol or cholesterol derivative in combination with a sphingoid or sphingolipid. In one embodiment, the sphingoid or sphingolipid is a ceramide and/or is a phytospingosine.

In another embodiment, the at least one oil and/or fat is a hydrocarbon. Exemplary hydrocarbons include, but are not limited to, dodecane, petrolatum, mineral oil, squalane, squalene and paraffin, and mixtures thereof. In one embodiment, the hydrocarbon is petrolatum, or a mixture of petrolatum and another oil or fat. In another embodiment, the hydrocarbon is a mixture of petrolatum and a second hydrocarbon. In another embodiment, the hydrocarbon is a mixture of mineral oil and a second hydrocarbon. In yet another embodiment, the hydrocarbon is a mixture of petrolatum and squalane. In yet another embodiment, the hydrocarbon is a mixture of mineral oil and squalane. In yet another embodiment, the hydrocarbon is a mixture of petrolatum and mineral oil.

Squalane helps enhance the skin's natural barrier function, protect the skin against the elements, and boost the skin's ability to retain moisture. Squalane is a component of human stratum corneum. Squalane is available in purified form (see e.g. Fitoderm® available from BASF) and may be used in the compositions in its purified form. Alternatively, an oil which is rich in squalane may be used.

Exemplary sources of squalane useful in the present compositions include, but are not limited to, shark liver oil, olive oil, palm oil, wheat germ oil, amaranth oil, rice bran oil and sugar cane. It is understood that squalane from these sources of oils is considered a lipid component. In one embodiment, squalane isolated from olive oil is preferred.

Suitably, the squalane is present in the at least one lamellar membrane structure in an amount from about 0.05% to about 2% by weight, based on the total weight of the composition.

In yet another embodiment, the at least one oil and/or fat is an essential oil. Exemplary essential oils include, but are not limited to, primrose oil, rose oil, *eucalyptus* oil, borage oil, bergamot oil, chamomile oil, citronella oil, lavender oil, peppermint oil, pine oil, pine needle oil, spearmint oil, tea tree oil and wintergreen oil, and mixtures thereof.

In a further embodiment, the at least one oil and/or fat is a vegetable oil. Exemplary vegetable oils include, but are not limited to, olus (vegetable) oil, almond oil, aniseed oil, canola oil, castor oil, coconut oil, corn oil, avocado oil, cottonseed oil, olive oil, palm kernel oil, peanut oil, sunflower oil, safflower oil and soybean oil, including hydrogenated and non-hydrogenated versions thereof, and mixtures thereof.

In yet a further embodiment, the at least one oil and/or fat is an edible oil. Exemplary edible oils include, but are not limited to, cinnamon oil, clove oil, lemon oil and peppermint oil, and mixtures thereof.

In an embodiment the oil is a fatty acid, a source of fatty acids, or an ester of glycerin as described herein. In an embodiment, the source of fatty acids is olus (vegetable) oil, olive oil or rice bran oil.

Suitably, the discontinuous oil phase is present in an amount from about 5% to about 70% by weight, based on the total weight of the composition. In an embodiment, the discontinuous oil phase is present in an amount from about 5% to about 50% by weight, based on the total weight of the composition. In another embodiment, the discontinuous oil phase is present in an amount from about 5% to about 45% by weight, based on the total weight of the composition. In yet another embodiment, the discontinuous oil phase is present in an amount from about 5% to about 35% by weight, based on the total weight of the composition.

In one embodiment, the oil phase does not contain maleated soybean oil. In another embodiment the oil phase does not contain from about 0 to about 30% of maleated soybean oil.

Aqueous Phase

The compositions of the invention comprise a continuous aqueous phase. The aqueous phase comprises water. Any additional components which are water miscible will be dissolved in this aqueous phase.

Suitably, the continuous aqueous phase is present in an amount from about 10% to about 90% by weight, based on the total weight of the composition. In an embodiment, the continuous aqueous phase is present in an amount from about 25% to about 90% by weight, based on the total weight of the composition. In another embodiment, the continuous aqueous phase is present in an amount from about 10% to about 70% by weight, based on the total weight of the composition. In another embodiment, the continuous aqueous phase is present in an amount from about 25% to about 75% by weight, based on the total weight of the composition. In another embodiment, the continuous aqueous phase is present in an amount from about 45% to about 90% by weight, based on the total weight of the composition. In yet another embodiment, the continuous aqueous phase is present in an amount from about 50% to about 90% by weight, based on the total weight of the composition. In a further embodiment, the continuous aqueous phase is present in an amount from about 60% to about 90% by weight, based on the total weight of the composition. In yet another embodiment, the continuous aqueous phase comprises water in an amount from about 35% to about 80% by weight, based on the total weight of the composition. In yet another embodiment, the continuous aqueous phase comprises water in an amount from about 40% to about 75% by weight, based on the total weight of the composition.

In an embodiment, the continuous aqueous phase comprises glycerin. In another embodiment, the glycerin is present in an amount from about 1% to about 40% by weight, based on the total weight of the composition. In another embodiment, the continuous aqueous phase comprises glycerin in an amount from about 5% to about 15% by weight, based on the total weight of the composition. In yet another embodiment, the continuous aqueous phase comprises glycerin in an amount of about 10% by weight, based on the total weight of the composition.

In one embodiment, the continuous aqueous phase may also include a sugar alcohol. Suitable sugar alcohols can include but are not limited to glucose, glycerol, sorbitol, mannitol, maltitol, galactitol, erythritol, xylitol, inositol, lactitol, and mixtures thereof. In one embodiment, the sugar alcohol is glucose. The sugar alcohol may be present in an amount from about 1% to about 20% by weight, based on the total weight of the composition.

The continuous aqueous phase may further comprise other water miscible components; such as for example, water miscible thickening agents, humectants and pH adjusting agents.

Thickening Agent

The compositions of the invention comprise at least one thickening agent or rheology modifier. In an embodiment, the thickening agent is a mixture of two or more thickening agents.

The function of the thickening agent is to stabilize the discontinuous oil phase of the composition. The thickening agent may also provide hardness and structural support useful in forming a stick composition, for example. Thickening agents may be water miscible which are used to thicken the aqueous portion of the emulsion composition. Other thickening agents are nonaqueous making them suitable for thickening the oil phase of the emulsion composition. Yet other thickening agents such as those described below, may act at the oil-water interface and thus lie at the interphase boundary.

Exemplary water miscible thickening agents include, but are not limited to, a cellulose derivative such as carboxymethylcellulose, hydroxyethylcellulose, hydroxypropylcellulose or hydroxypropyl methylcellulose; agar; carrageenan; curdlan; gelatin; gellan; β-glucan; tragacanth gum; guar gum; gum arabic; locust bean gum; pectin; starch; a carbomer; and xanthan gum or a xanthan gum derivative such as dehydroxanthan gum; salts thereof, and mixtures thereof. In yet another embodiment, the thickening agent is a carbomer or a salt thereof, such as sodium carbomer. In a further embodiment, the thickening agent is hydroxyethylcellulose.

Exemplary nonaqueous thickening agents include, but are not limited to, acrylate copolymers, VP/Eicosene copolymer, waxes, fatty alcohols and fatty acids.

In one embodiment, the thickening agent is a fatty alcohol such as described above in the oil phase. Suitable fatty alcohols include, but are not limited to, behenyl alcohol, isostearyl alcohol, caprylyl alcohol, decyl alcohol, lauryl alcohol, myristyl alcohol, lanolin alcohol, arachidyl alcohol, oleyl alcohol, palm alcohol, isocetyl alcohol, cetyl alcohol, stearyl alcohol and cetearyl alcohol, and mixtures thereof. Other suitable fatty alcohols include, but are not limited to, tridecyl alcohol, pentadecyl alcohol, isocetyl alcohol, palmitoleyl alcohol, heptadecyl alcohol, isostearyl alcohol, oleyl alcohol, nonadecyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, and lanolin alcohol, and mixtures thereof.

In one embodiment, the thickening agent is a fatty acid which may be saturated or unsaturated, branched or straight chained), or a source of fatty acids, and mixtures thereof.

Suitable fatty acids include those mentioned above in the oil phase, and also include but are not limited to, isostearic acid, linoleic acid, linolenic acid, oleic acid, myristic acid, ricinoleic acid, columbinic acid, arachidic acid, arachidonic acid, lignoceric acid, nervonic acid, eicosapentanoic acid, palmitic acid, stearic acid and behenic acid, and mixtures thereof. In one embodiment the fatty acid is behenic acid.

Other exemplary fatty acids include, but are not limited to lauric acid, tridecylic acid, myristic acid, pentadecylic acid, margaric acid, oleic acid, nonadecylic acid, arachidic acid, arachidonic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid and hexatriacontylic acid, and mixtures thereof.

In one embodiment, the thickening agent comprises a mixture of one or more of a fatty alcohol, a cellulose derivative, a xanthan derivative, a non-aqueous agent, and a carbomer. In one embodiment, the thickening agent mixture may comprise one or more of behenyl alcohol, dehydroxanthan gum, VP/Eicosene copolymer, acrylates/C10-30 alkyl acrylate cross polymer and sodium carbomer. In an embodiment, the thickening agent is a mixture of polyacrylate crosspolymer-6 and hydroxyethyl acrylate/sodium acryloyldimethyl taurate copolymer.

In an embodiment, the thickening agent is an acrylate copolymer, such as acrylates/C10-30 alkyl acrylate cross polymer, polyacrylate crosspolymer-6, or a mixture of hydroxyethyl acrylate and sodium acryloyldimethyl taurate copolymer.

In one embodiment, the thickening agent is polyacrylate crosspolymer-6. Polyacrylate crosspolymer-6 is available as "Sepimax Zen" from Seppic, a subsidiary of Air Liquide Group.

In another embodiment, the thickening agent is a mixture of hydroxyethyl acrylate and sodium acryloyldimethyl taurate copolymer. A mixture of hydroxyethyl acrylate and sodium acryloyldimethyl taurate copolymer is available as "Sepinov Weo" from Seppic, a subsidiary of Air Liquide Group.

In yet another embodiment, the thickening agent is a mixture of polyacrylate crosspolymer-6 and hydroxyethyl acrylate/sodium acryloyldimethyl taurate copolymer.

In one embodiment, the thickening agent is xanthan gum. In another embodiment, the thickening agent is dehydroxanthan gum. In yet another embodiment, the thickening agent is a carbomer or a salt thereof, such as sodium carbomer. In a further embodiment, the thickening agent is hydroxyethylcellulose.

Suitably, the thickening agent is present in an amount from about 0.1% to about 10% by weight, based on the total weight of the composition. In an embodiment, the thickening agent is present in an amount from about 0.2% to about 5% by weight, based on the total weight of the composition. In another embodiment, the thickening agent is present in an amount from about 0.2% to about 2% by weight, based on the total weight of the composition.

Lamellar Membrane Structure

The compositions of the invention comprise at least one lamellar membrane structure. Generally this refers to a planar lipid bilayer sheet, or a slight curve around a droplet of oil. They may also exist as separate discrete lamellae in the bulk aqueous phase. This is in contrast to a rounded formed liposomal structure. In another embodiment, the respective lamellar membrane structures form two or more stacked lamellar membrane structures, sometimes referenced as a liquid crystal. Two lamellar membrane structures stacked together, one on top of the other, is known as a double lamellar membrane structure.

FIG. 1 illustrates the key physical difference between an oil in water emulsion that can form a lamellar structure (A) and a liposome (B). In an O/W emulsion the surfactant-emulsifiers orientate so that the hydrophilic heads face out into the continuous phase and the hydrophobic tails are anchored within the oil droplet. In the case of a liposome, these are typically aqueous filled cores where the hydrophilic heads of the interfacial layer of surfactant-emulsifer (here shown as a dialkyl phospholipid which can form liposomal structures) orientated toward the hydrophilic aqueous core and for the outermost layer, orientated towards the continuous phase.

Even if systems contain lamellar forming ingredients such as those further described herein, those systems can be prepared in a manner that will yield either a liposome or O/W emulsion. The physical characteristics of each system is different and is outlined below.

| Property | O/W Emulsion | Aqueous Core Liposome |
|---|---|---|
| Droplet size | Typically >1000 nm | Range from 25 nm to 500 nm |
| Opacity | Very often white in appearance due to greater interaction with visible light. | Can be translucent to blue due to wavelength of light absorption/reflection |
| Rheology/Viscosity | Mid to high viscosity system (attributable to long range interactions between droplets) | Tend towards low viscosity systems (limited long range interactions between systems) |
| Dynamic Lamellar Structure (Viscosity Building) | Viscosity can build post manufacture due to thermodynamic equilibration. Lamellar structure builds with time causing an increase in viscosity. | Viscosity is relatively stable as lamellar liposomal structure has been established during the manufacturing process. |

The properties described above are measurable using standard lab measurement methods available in the art. All of these properties will clearly provide for an accurate designation of those O/W emulsions (microscopy, rheology, visual assessment) having lamellar structures (e.g. with FTIR/XRD).

According to the invention, the at least one lamellar membrane structure comprises (i) a phospholipid and (ii) a fatty alcohol.

In another embodiment, the at least one lamellar membrane structure comprises (i) a phospholipid, (ii) a fatty alcohol, and (iii) an ester of a fatty acid and a fatty alcohol.

According to the invention, the at least one lamellar membrane structure comprises (i) a phospholipid and (ii) a fatty alcohol; and (iii) an ester of a branched fatty acid and a branched fatty alcohol.

In another embodiment, the at least one lamellar membrane structure comprises (i) a phospholipid, (ii) fatty acid and (iii) an ester of a fatty acid and a fatty alcohol.

In another embodiment, the at least one lamellar membrane structure comprises (i) a phospholipid, (ii) fatty alcohol and (iii) a fatty acid.

In another embodiment, the at least one lamellar membrane structure comprises (i) a phospholipid, (ii) a fatty alcohol, (iii) a fatty acid, and (iv) and an ester of a fatty acid and a fatty alcohol. In one embodiment the ester is of a branched fatty acid and a branched fatty alcohol.

In yet another embodiment the at least one lamellar membrane structure comprising any of these above components, in use, has a water vapor transmission rate of less than about 70 $g \cdot m^2 \cdot hr^{-1}$ measured in vitro using the modWVTR test methodology as further described herein.

In one embodiment, when the lamellar blend contains a fatty alcohol of $C_{16}$-18 chain length (branched or straight chain), it may also comprise and a second fatty alcohol (branched or straight chain). Suitably the second fatty alcohol is of $C_{22}$-$C_{36}$ carbon atom length.

Suitably, the components of the lamellar membrane structure are present in an amount from about 2.5% to about 20% by weight, based on the total weight of the composition. In an embodiment, the components of the lamellar membrane structure are present in an amount from about 3% to about 15% by weight, based on the total weight of the composition. In another embodiment, the components of the lamellar membrane structure are present in an amount of about 3%, 4%, 5%, 6%, 7%, 8%, 9%, 10%, 11%, 12%, 13%, 14% or 15% by weight, based on the total weight of the composition.

Suitably, the components of the lamellar membrane structure are present in an amount from about 1 to about 20% by weight, based on the total weight of the composition. In another embodiment, the one lamellar membrane structurant is present in an amount from about 1 to about 15% by weight. In another embodiment, the components of the lamellar membrane structure are present in an amount of about 8 to about 10%, by weight, based on the total weight of the composition. In yet another embodiment, the components of the lamellar membrane structure are present in an amount of about 8.8% by weight, based on the total weight of the composition.

In another embodiment, the at least one lamellar membrane structure comprises a (i) a phospholipid, (ii) a fatty alcohol, (iii) a fatty acid, and (iv) an ester of a branched fatty acid and a branched fatty alcohol and squalane.

In another embodiment, the at least one lamellar membrane structure comprises a (i) a phospholipid, (ii) a fatty alcohol, (iii) a fatty acid, and (iv) an ester of a branched fatty acid and a branched fatty alcohol and at least one of rice bran oil and/or rice bran wax.

In another embodiment, the at least one lamellar membrane structure comprises a (i) a phospholipid, (ii) a fatty alcohol, (iii) a fatty acid, and (iv) an ester of a branched fatty acid and a branched fatty alcohol, and at least one of a phytosterol, squalane, rice bran oil and/or rice bran wax. In yet a further embodiment, the at least one lamellar membrane structure further comprises a ceramide.

In another embodiment, the at least one lamellar membrane structure comprises a (i) a phospholipid, (ii) a fatty alcohol, (iii) a fatty acid, and (iv) an ester of a branched fatty acid and a branched fatty alcohol at least one of a phytosterol, squalane, rice bran oil, rice bran wax, and a sphingolipid or a sphingolipid mimic.

In another embodiment, the at least one lamellar membrane structure comprises a (i) a phospholipid, (ii) a fatty alcohol, (iii) a fatty acid, and (iv) an ester of a branched fatty acid and a branched fatty alcohol, a phytosterol, and optionally at least one of squalane, rice bran oil, rice bran wax, pentylene glycol, and a sphingolipid or a sphingolipid mimic.

In another embodiment, the at least one lamellar membrane structure comprises a (i) a phospholipid, (ii) a fatty alcohol, (iii) a fatty acid, and (iv) an ester of a fatty acid and a fatty alcohol, and at least one of rice bran oil, rice bran wax, squalane, a phytosterol, cholesterol or cholesterol derivative, a sphingolipid or a sphingolipid mimic, or a triglyceride. In one embodiment, the ester is of a branched fatty acid and a branched fatty alcohol.

Many of the lipids used in the present compositions are the same or similar to the lipids found in human stratum corneum.

Phospholipid

The compositions of the invention comprise a phospholipid. Suitably, the phospholipid is selected from the group consisting of lecithin, hydrogenated lecithin, phosphatidylcholine and hydrogenated phosphatidylcholine, and mixtures thereof.

In one embodiment, the phospholipid is lecithin. In another embodiment, the phospholipid is hydrogenated lecithin. In yet another embodiment, the phospholipid is phosphatidylcholine. In a further embodiment, the phospholipid is hydrogenated phosphatidylcholine.

In yet a further embodiment, the phospholipid is hydrogenated lecithin or hydrogenated phosphatidylcholine. In one embodiment, the phospholipid is a mixture of phosphatidylcholine and hydrogenated phosphatidylcholine.

In an embodiment, the phospholipid is present in an amount from about 0.5% to about 5% by weight, based on the total weight of the composition. In another embodiment, the phospholipid is present in an amount from about 0.5% to about 2.5% by weight, based on the total weight of the composition.

Fatty Alcohol

The lamellar membrane structure comprises a fatty alcohol. In an embodiment, the fatty alcohol is a branched or straight chain, saturated or unsaturated $C_{12}$-$C_{36}$ fatty alcohol. In another embodiment, the fatty alcohol is a $C_{14}$-$C_{26}$ fatty alcohol. In one embodiment, the chain is of $C_{16}$ to $C_{22}$ carbon atoms. In another, the chain is of $C_{18}$-$C_{30}$ carbon atoms. In a further embodiment, the chain is of $C_{20}$-$C_{26}$ carbon atoms. In yet another embodiment, the chain is of $C_{20}$-$C_{30}$ carbon atoms. In a further embodiment, the chain is of $C_{22}$ to $C_{28}$ carbon atoms. In another embodiment, the fatty alcohol is a branched or straight chain, saturated or unsaturated $C_{18}$ or $C_{20}$ or $C_{22}$ or $C_{24}$ carbon atoms. In yet a further embodiment, the fatty alcohol is a branched or straight $C_{22}$ fatty alcohol. In another embodiment, the fatty alcohol is a branched chain fatty alcohol. In another embodiment, the fatty alcohol is a straight chain fatty alcohol. In an embodiment, the fatty alcohol is a mixture of two or more fatty alcohols.

In one embodiment, the fatty alcohol is a branched chain fatty alcohol. In another embodiment, the fatty alcohol is a straight chain fatty alcohol. The mixture may be a combination of branched, straight, unsaturated and saturated fatty alcohols. In another embodiment, the fatty alcohol is a mixture of at least two fatty alcohols of differing chain lengths.

Exemplary straight chain fatty alcohols for use in the invention include all of those mentioned above under the oil phase and the thickening agents and further include but are not limited to, lauryl alcohol (Cu), tridecyl alcohol ($C_{13}$), myristyl alcohol ($C_{14}$), pentadecyl alcohol ($C_{15}$), cetyl alcohol ($C_{16}$), cetearyl alcohol ($C_{16}$/$C_{18}$), palmitoleyl alcohol ($C_{16}$), heptadecyl alcohol ($C_{17}$), stearyl alcohol ($C_{18}$), nonadecyl alcohol ($C_{19}$), arachidyl alcohol ($C_{16}$), heneicosyl alcohol ($C_{21}$), behenyl alcohol ($C_{22}$), erucyl alcohol ($C_{22}$), lignoceryl alcohol ($C_{24}$), ceryl alcohol ($C_{26}$), 1-heptacosanol ($C_{27}$), montanyl alcohol ($C_{28}$), 1-nonacosanol ($C_{29}$), myricyl alcohol ($C_{30}$), lacceryl alcohol ($C_{32}$), geddyl alcohol ($C_{34}$) and tetratriacontanol ($C_{36}$), and mixtures thereof.

In one embodiment, the fatty alcohols include, but are not limited to, behenyl alcohol, isostearyl alcohol, caprylyl alcohol, decyl alcohol, lauryl alcohol, myristyl alcohol, lanolin alcohol, lignoceryl alcohol, arachidyl alcohol, oleyl alcohol, palm alcohol, isocetyl alcohol, cetyl alcohol, stearyl alcohol and cetearyl alcohol, and mixtures thereof.

In an embodiment, the straight chain fatty alcohol is cetyl alcohol ($C_{18}$).

In one embodiment, the straight chain fatty alcohol is behenyl alcohol ($C_{22}$).

In another embodiment, the straight chain fatty alcohol is a mixture of cetyl alcohol ($C_{16}$) and behenyl alcohol ($C_{22}$).

In an embodiment, the straight chain fatty alcohol is a $C_{12}$-$C_{36}$ straight chain fatty alcohol. In another embodiment, the straight chain fatty alcohol is a $C_{14}$-$C_{26}$ straight chain fatty alcohol. In yet another embodiment, the straight chain fatty alcohol is a $C_{16}$-$C_{22}$ straight chain fatty alcohol. In another embodiment, the straight chain fatty alcohol is a $C_{18}$-$C_{230}$ straight chain fatty alcohol. In another embodiment, the straight chain fatty alcohol is a $C_{20}$-$C_{30}$ straight chain fatty alcohol. In another embodiment, the straight chain fatty alcohol is a $C_{22}$-$C_{28}$ straight chain fatty alcohol. In yet a further embodiment, the straight chain fatty alcohol is a $C_{20}$ or $C_{22}$ or $C_{24}$ straight chain fatty alcohol. In yet a further embodiment, the straight chain fatty alcohol is a $C_{24}$ straight chain fatty alcohol.

In one embodiment, the fatty alcohol is present in an amount from about 2% to about 15% by weight, based on the total weight of the composition. In another embodiment, the fatty alcohol is present in an amount from about 2% to about 10% by weight, or from about 2% to about 7.5% by weight, based on the total weight of the composition.

In an embodiment, the fatty alcohol and the phospholipid are present in a weight ratio from about 10:1 to about 1:1. In another embodiment, the fatty alcohol and the phospholipid are present in a weight ratio from about 8:1 to about 2:1. In yet another embodiment, the fatty alcohol and the phospholipid are present in a weight ratio from about 5:1 to about 4:1.

Fatty Acid

In an embodiment, the lamellar membrane structure further comprises a fatty acid. In an embodiment, the fatty acid is a mixture of two or more fatty acids.

In an embodiment, the fatty acid is a $C_{12}$-$C_{36}$ fatty acid which may be saturated or unsaturated, branched or straight chained. In one embodiment, the branched or straight chain is $C_{16}$-$C_{26}$ carbon atoms. In another embodiment the branched or straight chain is $C_{12}$-$C_{22}$ carbon atoms. In another, the branched or straight chain is $C_{18}$-$C_{36}$ carbon atoms. In another, the branched or straight chain is $C_{18}$-$C_{30}$ carbon atoms. In another embodiment, the branched or straight chain is $C_{20}$-$C_{30}$ carbon atoms. In yet another embodiment, the branched or straight chain is $C_{20}$-$C_{28}$ carbon atoms. In a further embodiment, the branched or straight chain is $C_{20}$-$C_{26}$ carbon atoms. In a further embodiment, the branched or straight chain is $C_{22}$-$C_{28}$ carbon atoms. In yet another embodiment, the branched or straight chain is $C_{22}$-$C_{30}$ carbon atoms. In yet further embodiment, the fatty acid is a branched or straight $C_{22}$ or a $C_{24}$ chain.

In one embodiment, the fatty acid is a straight chain fatty acid. In one embodiment, the fatty acid is an unsaturated straight chain fatty acid.

In an embodiment, the straight chain fatty acid is a $C_{12}$ to $C_{36}$ straight chain fatty acid. In an embodiment, the straight chain fatty acid is a $C_{16}$ to $C_{36}$ straight chain fatty acid. In another embodiment, the straight chain fatty acid is a $C_{12}$-$C_{22}$ straight chain fatty acid. In an embodiment, the straight chain fatty acid is a $C_{18}$ to $C_{36}$ straight chain fatty acid. In an embodiment, the straight chain fatty acid is a $C_{18}$ to $C_{30}$ straight chain fatty acid. In yet another embodiment, the straight chain fatty acid is a $C_{20}$-$C_{30}$ straight chain fatty acid. In a further embodiment, the straight chain fatty acid is a $C_{20}$-$C_{28}$ straight chain fatty acid. In an embodiment, the straight chain fatty acid is a $C_{20}$ to $C_{26}$ straight chain fatty acid. In yet a further embodiment, the straight chain fatty acid is a $C_{22}$ or a $C_{24}$ straight chain fatty acid.

Exemplary straight chain fatty acids for use in the lamellar membrane structure include, but are not limited to, lauric acid ($C_{12}$), tridecylic acid ($C_{13}$), myristic acid ($C_{14}$), pentadecylic acid ($C_{15}$), palmitic acid ($C_{16}$), margaric acid ($C_{17}$), stearic acid ($C_{18}$), nonadecylic acid ($C_{19}$), arachidic acid ($C_{20}$), heneicosylic acid ($C_{21}$), behenic acid ($C_{22}$), tricosylic acid ($C_{23}$), lignoceric acid ($C_{24}$), pentacosylic acid ($C_{25}$), cerotic acid ($C_{26}$), heptacosylic acid ($C_{27}$), montanic acid ($C_{28}$), nonacosylic acid ($C_{29}$), melissic acid ($C_{30}$), henatriacontylic acid ($C_{31}$), lacceroic acid ($C_{32}$), psyllic acid ($C_{33}$), geddic acid ($C_{34}$), ceroplastic acid ($C_{35}$) and hexatriacontylic acid ($C_{36}$), and mixtures thereof.

In one embodiment, the straight chain fatty acid is behenic acid ($C_{22}$).

Other exemplary fatty acids include, but are not limited to, isostearic acid (also known as isoactadecanoic acid) (C18), linoleic acid (C18), linolenic acid (C18), oleic acid (C18), myristic acid (also known as tetradecanoic acid) (C14), ricinoleic acid (C18), columbinic acid (C18), arachidic acid (also known as eicosanoic acid) (C20), arachidonic acid (C20), lignoceric acid (also known as tetracosanoic acid) (C24), nervonic acid (C24), eicosapentanoic acid (C20), palmitic acid (also known as hexadecanoic acid) (C16), and mixtures thereof.

Fatty acids suitable for use herein can be obtained from natural sources. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, and mixtures thereof. The fatty acids can also be synthetically prepared. Fatty acids can also be prepared from mixtures of natural or synthetic wax esters by use of appropriate synthetic chemistry. Examples include Rice Bran Wax, etc.

In an embodiment, the phospholipid and the fatty acid are present in a weight ratio from about 5:1 to about 1:5. In another embodiment, the phospholipid and the fatty acid are present in a weight ratio from about 2:1 to about 1:2. In yet another embodiment, the phospholipid and the fatty acid are present in a weight ratio from about 2:1 to about 1:1.

In an embodiment, the fatty alcohol and the fatty acid are present in a weight ratio from about 10:1 to about 1:1. In another embodiment, the fatty alcohol and the fatty acid are present in a weight ratio from about 8:1 to about 4:1.

In another embodiment, the fatty acid is present in an amount from about 0.1% to about 5% by weight, based on the total weight of the composition. In another embodiment, the fatty acid is present in an amount from about 0.25% to about 2.5% by weight, or from about 0.5% to about 2.5% by weight, based on the total weight of the composition.

The fatty alcohol and the fatty acid may react to form an ester when both are present in the composition. In an embodiment, the ester, when formed, is a cetyl behenate and/or behenyl behenate.

Ester of a Fatty Acid and a Fatty Alcohol

In an embodiment, the lamellar membrane structure further comprises an ester of a branched or straight chain fatty acid and a branched or straight chain fatty alcohol ("the ester"). It is recognized that because there are two components to the ester, either one or both of them can be branched or straight chained components, e.g. the ester can be mixed. For example, the fatty acid component may be branched and the fatty alcohol may be straight chained. Alternatively, the fatty acid component may be straight chained and the fatty alcohol may be branched. In another embodiment, both the acid and the alcohol may be branched. In yet another embodiment both the acid and the alcohol may be straight chained.

In an embodiment, the ester comprises a mixture of compounds having mono- and poly-branching in the acid and alcohol originating parts of the ester. In one embodiment, the fatty acid and fatty alcohol are alkyl branched.

In an embodiment, when the composition comprises an ester of a branched or straight chain fatty acid and a branched or straight chain fatty alcohol, the composition may further comprise a fatty acid.

In an embodiment, the branched fatty acid component of the ester is a $C_{12}$ to $C_{36}$ branched fatty acid, a $C_{12}$ to $C_{30}$ branched fatty acid, a $C_{14}$ to $C_{26}$ branched fatty acid, a $C_{16}$ to $C_{22}$ branched fatty acid, or a $C_{18}$ branched fatty acid.

Fatty acids suitable for use in the ester can be obtained from natural sources or can also be synthetically prepared. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used as a basis for chemical modification.

Fatty acids suitable for use in the ester can be obtained from natural sources or can also be synthetically prepared. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. Or they could have come from mixtures of wax esters that have been modified to be predominantly fatty acid mixtures (ester hydrolysis). The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used as a basis for chemical modification.

Exemplary branched fatty acids for use in the ester include, but are not limited to, iso-acids such as isostearic acid, isopalmitic acid, isomyristic acid, isoarachidic acid and isobehenic acid, neo-acids such as neodecanioc acid, and/or anti-iso acids. In one embodiment, the branched fatty acid for use in the ester is isostearic acid.

In an embodiment, the branched fatty alcohol component of the ester is a $C_{12}$ to $C_{36}$ branched fatty alcohol, a $C_{12}$ to $C_{30}$ branched fatty alcohol, a $C_{14}$ to $C_{26}$ branched fatty alcohol, a $C_{16}$ to $C_{22}$ branched fatty alcohol, or a $C_{18}$ branched fatty alcohol.

In another embodiment, the ester is an ester of a $C_{16}$ to $C_{22}$ branched fatty acid and a $C_{16}$ to $C_{22}$ branched fatty alcohol. The branched fatty acid and branched fatty alcohol may comprise the same number of carbon atoms, or a different number of carbon atoms. In one embodiment, the branched fatty acid and branched fatty alcohol comprise the same number of carbon atoms.

The ester may comprise one or more variations selected from the group comprising mono-branched fatty acid and poly-branched fatty alcohol, mono-branched fatty acid and mono-branched fatty alcohol, poly-branched fatty acid and mono-branched fatty alcohol, and poly-branched fatty acid and poly-branched fatty alcohol. The ester may be selected from this group by any suitable separation method. For example, the selected ester may be selected from a mixture of esters using a clathration method.

Exemplary branched fatty alcohols for use in the ester include, but are not limited to iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the fatty alcohol for use in the ester is isostearyl alcohol.

In an embodiment, the ester is an ester of a $C_{12}$ to $C_{36}$ branched or straight chain fatty acid and a $C_{12}$ to $C_{36}$ branched or straight chain fatty alcohol. In one embodiment, the fatty acid and the fatty alcohol are both branched. In another embodiment, the ester is an ester of a $C_{16}$ to $C_{30}$ branched fatty acid and a $C_{16}$ to $C_{30}$ branched fatty alcohol. In one embodiment, the fatty acid and the fatty alcohol are both branched.

In one embodiment, the ester comprises a $C_{18}$ mono- and/or poly-branched fatty acid and a $C_{18}$ mono- and/or poly-branched fatty alcohol.

In an embodiment, the ester is isostearyl isostearate ("ISIS").

In another embodiment, the ester is an ester of a $C_{16}$ to $C_{30}$ straight chain fatty acid and a $C_{16}$ to $C_{30}$ straight chain fatty alcohol.

In an embodiment, the ester is heptadecanoyl heptadecanoate ("HDHD").

Suitably, the ester is present in the lamellar membrane blend in an amount from about 0.1% to about 75% by weight. In an embodiment, the ester is present in an amount of about 1% to about 50% by weight. In another embodiment, the ester is present from about 5% to about 50% by weight. In another embodiment, the ester is present from about 5% to about 35% by weight based on the total weight of the lamellar membrane blend. In one embodiment, the ester is present in the lamellar membrane blend in an amount from about 1% to about 25% by weight, based on the total weight of the lamellar membrane blend. In one embodiment the ester is present in an amount from about 0.1% to about 5% by weight, based on the total weight of the composition. In another embodiment the ester is present in an amount from about 1% to about 5% by weight, based on the total weight of the composition.

In an embodiment, the phospholipid and the ester are present in a weight ratio from about 5:1 to about 1:5. In another embodiment, the phospholipid and the ester are present in a weight ratio from about 2:1 to about 1:2. In yet another embodiment, the phospholipid and the ester are present in a weight ratio from about 2:1 to about 1:1.

In an embodiment, the fatty alcohol and the ester are present in a weight ratio from about 10:1 to about 1:1. In another embodiment, the fatty alcohol and the ester are present in a weight ratio from about 8:1 to about 4:1.

In an embodiment, the fatty acid and the ester are present in a weight ratio from about 5:1 to about 1:5. In yet another embodiment, the fatty acid and the ester are present in a weight ratio from about 2:1 to about 1:2. In a further embodiment, the fatty acid and the ester are present at a weight ratio of about 1:1.

In an embodiment, the ester is present in an amount from about 0.1% to about 5% by weight, based on the total weight of the composition. In one embodiment, the ester is present in an amount from about 0.25% to about 2.5% by weight, or from about 0.5% to about 2.5% by weight, based on the total weight of the composition.

In a further embodiment, the weight ratio of phospholipid:fatty alcohol:fatty acid:ester is about 1.4:6.4:1:1.

Dermatologically Acceptable Excipients

The compositions of the invention may further comprise at least one dermatologically acceptable excipient.

In an embodiment, the dermatologically acceptable excipient is selected from the group consisting of an antioxidant, a chelating agent, a preservative, a moisturizer, a humectant and a pH adjusting agent, and mixtures thereof.

In an embodiment, the compositions of the invention are free or substantially free of a conventional emulsifier.

Antioxidant

The compositions of the invention may further comprise an antioxidant. In an embodiment, the antioxidant is a mixture of two or more antioxidants.

Antioxidants may protect the composition from oxidation (e.g. becoming rancid) and/or may also provide lip conditioning benefits upon application to the lips. Tocopherol, tocopheryl acetate, some botanical butters, niacinamide, pterostilbene (trans-3,5-dimethoxy-4-hydroxystilbene) magnolol, and green tea extracts, alone or in combination thereof are exemplary natural product antioxidants suitable for use in the compositions. Other suitable antioxidants include ascorbic acid and esters thereof such as ascorbyl palmitate, butylated hydroxytoluene (BHT), butylated hydroxyanisole (BHA), propyl gallate, vitamin E TPGS, ethyl ferulate, ferulic acid, resveratrol, 2,2-dimethyl chroman (Lipochroman®), singapine, tetrahydrocurcumin or other curcumin derivatives, hydroxytyrosol, Bis-Ethylhexyl Hydroxydimethoxy Benzylmalonate (Ronacare AP®), dimethylmethoxy chromanyl palmitate (Chromabright®) or a combination or mixture thereof. It is recognized that a combination or mixture of all of these antioxidants is also suitable for use herein. In one embodiment, the antioxidant is tocopherol, or a mixture of tocopherol and ascorbyl palmitate. In another embodiment, the antioxidant is niacinamide.

Suitably, the antioxidant is present in an amount from about 0.001% to about 1% by weight, based on the total weight of the composition.

Chelating Agents

The compositions of the invention may further comprise a chelating agent. In an embodiment, the chelating agent is a mixture of two or more chelating agents.

Exemplary chelating agents include, but are not limited to, citric acid, glucuronic acid, sodium hexametaphosphate, zinc hexametaphosphate, ethylenediamine tetraacetic acid (EDTA), ethylenediamine disuccinic acid (EDDS), phosphorates, salts thereof, or a combination or mixture thereof.

In one embodiment, the chelating agent is EDTA or a salt thereof, such as potassium, sodium or calcium salts of EDTA. In another embodiment, the chelating agent is EDDS or a salt thereof, such as potassium, sodium or calcium salts of EDDS.

In one embodiment, the chelating agent is trisodium ethylenediamine disuccinate.

Suitably, the chelating agent is present in an amount from about 0.05% to about 1% by weight, based on the total weight of the composition.

Preservative

The compositions of the invention may further comprise a preservative. In an embodiment, the preservative is a mixture of two or more preservatives.

Exemplary preservatives include, but are not limited to, benzyl alcohol, diazolidinyl urea or other substituted ureas and hydantoin derivatives, methyl paraben, ethyl paraben, propyl paraben, butyl paraben, phenoxyethanol, sorbic acid, benzoic acid, propylene glycol, pentylene glycol, hexylene glycol, salts thereof, or a combination or mixture thereof.

In an embodiment, the preservative is a combination of non-conventional preservatives, such as capryloyl glycine, 1,2-hexanediol and other glycols. Other suitable glycols include, but are not limited to, caprylyl glycol and/or pentylene glycol. In one embodiment, the preservative is a mixture of pentylene glycol and hexylene glycol.

Suitably, these preservatives are present in an amount from about 0.01% to about 5% by weight, based on the total weight of the composition. In another embodiment, the preservative is present in an amount from about 0.01% to about 2% by weight.

In one embodiment, the capryloyl glycine is present in an amount from about 0.5% to about 2% by weight and the additional glycols can be added in amounts up to 5% by weight, based on the total weight of the composition. Suitably, the preservative is a combination of at least capryloyl glycine and caprylyl glycol in an amount from about 0.5% to about 2% by weight, based on the total weight of the composition.

Moisturizer

The compositions of the invention may further comprise a moisturizer. Exemplary moisturizers useful in the present compositions include, but are not limited to, propylene glycol, dipropylene glycol, butylene glycol, pentylene glycol, hexylene glycol, polyethylene glycol, glycerin, sodium pyrrolidone carboxylate, α-hydroxy acids, β-hydroxy acids, ethoxylated and propoxylated polyols, polysaccharides, panthenol, sorbitol, hyaluronic acid and salts thereof, such as sodium, potassium or calcium salts, and mixtures thereof.

Suitably, the moisturizer is present in an amount from about 0.5% to about 10% by weight, based on the total weight of the composition.

Humectant

The compositions of the invention may further comprise a humectant. Exemplary humectants useful in the present compositions include, but are not limited to, glycerin, betaine, sarcosine, panthenol, propylene glycol, butylene glycol, pentylene glycol, hexylene glycol, caprylyl glycol, sorbitol and glucose, and mixtures thereof.

In one embodiment, the humectant is a mixture of glycerin and panthenol.

Suitably, the humectant is present in an amount from about 1% to about 15% by weight, based on the total weight of the composition.

pH Adjusting Agent

The compositions of the invention may further comprise a pH adjusting agent. In one embodiment, the pH adjusting agent is a base. Suitable bases include amines, bicarbonates, carbonates, and hydroxides such as alkali or alkaline earth metal hydroxides, as well as transition metal hydroxides. In an embodiment, the base is sodium hydroxide or potassium hydroxide.

In another embodiment, the pH adjusting agent is an acid, an acid salt, or mixtures thereof. Suitably, the acid is selected from the group consisting of lactic acid, acetic acid, maleic acid, succinic acid, citric acid, benzoic acid, boric acid, sorbic acid, tartaric acid, edetic acid, phosphoric acid, nitric acid, ascorbic acid, dehydroacetic acid, malic acid, propionic acid, sulphuric acid and hydrochloric acid, or a combination or mixture thereof.

In yet another embodiment, the pH adjusting agent is a buffer. Suitably, the buffer is selected from the group consisting of citrate/citric acid, acetate/acetic acid, phosphate/phosphoric acid, propionate/propionic acid, lactate/lactic acid, carbonate/carbonic acid, ammonium/ammonia and edetate/edetic acid, or a combination or mixture thereof Colorant The compositions of the invention may further comprise a colorant that imparts color to the composition. Colorants include, for example, natural colorants such as plant extracts, natural minerals, carmine, synthesized and/or processed colorant materials such as iron oxides, synthetic dyes, organic compounds, lake colorants, and FDA certified colorants for use on the skin. The above list is not an exhaustive list of colorants and those of skill in the art may consider the use of other colorants. Formulations of colorants are commercially available. An example of a commercially available colorant contains caprylic/capric triglycerides (59.5%), titanium dioxide (39.6%), castor oil phosphate (0.5%) and triethoxycaprylylsilane (0.4%).

Sensate

The compositions of the invention may further comprise a sensate. A sensate is a composition that initiates a sensory perception such as heating or cooling, for example, when contacted with the skin. Exemplary sensates include, but are not limited to, mint extracts, cinnamon extract and capsaicin. Preferred sensates are derived from natural sources. However, synthetic sensates are within the scope of this invention. Sensates typically have high potency and accordingly may yield significant impact at low levels. Suitably, the sensate is present in an amount from about 0.05% to about 5% by weight, based on the total weight of the composition.

Pharmaceutically Active Agent

The compositions of the invention may further comprise a pharmaceutically acceptable active agent. Exemplary active agents include, but are not limited to, an anti-inflammatory agent, an antibacterial agent, an antiviral agent, an antifungal agent, an anti-parasitic agent, a nutritional agent, a sunscreen, a sun block, and mixtures thereof. Suitably, the pharmaceutically active agent is present in an amount from about 0.001% to about 30% by weight, depending on the nature of the active agent, the condition being treated, and the composition.

In one embodiment, the pharmaceutically active agent is an anti-inflammatory agent. Exemplary anti-inflammatory agents are niacinamide and N-acylalkanolamines including, but not limited to, lactamide monoethanolamine (MEA), oleamide MEA, acetamide MEA (AMEA), palmitioyl MEA (PMEA), N-acetylphosphatidylethanolamine, N-acetylethanolamine, N-oleoylethanolamine, N-linolenoylethanolamine, N-acylethanolamine, and N-acyl-2-hydroxy-propylamine.

In one embodiment, the N-acylalkanolamine is palmitidyl MEA (PMEA).

Suitably, the N-acylalkanolamine is present in an amount from about 0.01% to about 2% by weight, based on the total weight of the composition.

In another embodiment, the anti-inflammatory agent is niacinamide.

Suitably, the niacinamide is present in an amount from about 0.01% to about 5% by weight, based on the total weight of the composition.

In another embodiment, the pharmaceutically active agent is a sunscreen. Suitably, the sunscreen is a UVA and/or UVB sunscreen. Suitably, the sunscreen is a combination of a UVA sunscreen and a UVB sunscreen.

Efficacious protection from UVA and UVB radiation requires the use of significant amounts of sunscreen, and often a mixture of organic sunscreens, to achieve efficacious protection from both UVA and UVB radiation. UVB radiation, which is radiation in the wavelength range of 290 nm-320 nm, has traditionally been characterized as the radiation that causes sunburn. In addition, UVB radiation can decrease enzymatic and non-enzymatic antioxidants in the skin and impair the natural protective mechanisms in the skin, thereby contributing to DNA damage and potentially skin cancer. The dangers of UVA radiation, which is radiation in the wavelength range of 320 nm to 400 nm, have only recently been recognized. Chronic exposure to UVA radiation can cause damage to gene P53 DNA, possibly leading to cancer. Additionally, the longer UVA wavelengths allow for relatively deep penetration into the skin tissues causing damage to the elastic fibers and collagen which give skin its shape, thus causing wrinkling and eventually premature skin aging. Thus, protecting the skin from UVA and UVB radiation is important for skin health and overall health more generally.

For purposes herein, wavelength range is as follows: UVA1: 340-400 nm, UVA2: 320-340 nm, and UVB: 290-. Suitable UVA1 and UVA2 filters include, but are not limited to, Avobenzone (Butyl methoxy dibenzoyl methane) (Parsol 1789, Eusolex 9020), Bisdisulizole disodium (Neo Heliopan AP), Diethylamino hydroxybenzoyl hexyl benzoate (Uvinul A Plus), Drometrizole trisiloxane (Mexoryl XL), Menthyl anthranilate (Meradimate), oxybenzone, sulisobenzene and dioxybenzone, and mixtures thereof.

UVB filters include, but are not limited to, Amiloxate, 4-Aminobenzoic acid (PABA), Cinoxate, Ethylhexyl triazone/octyltriazone (Uvinul T 150), Homosalate, 4-Methylbenzylidene camphor (Parsol 5000), Octyl methoxycinnamate (Octinoxate) (Parsol MCX), Octyl salicylate/ethylhexyl salicylate (Octisalate), Padimate O (Escalol 507), Phenylbenzimidazole sulfonic acid (Ensulizole), Polysilicone-15 (Parsol SLX), Enzacamene, and Trolamine salicylate, and mixtures thereof.

UVA+UVB filters include, but are not limited to, Bemotrizinol (Tinosorb S), Benzophenones 1-12, Dioxybenzone, Terephthalylidene dicamphor sulfonic acid (Ecamsule) (Mexoryl SX), Diethylhexyl butamido triazone/Iscotrizinol (Uvasorb HEB), Octocrylene, Oxybenzone (Eusolex 4360), Benzophenone-4(Sulisobenzone), Bisoctrizole (Tinosorb M), Heliolex (a combination of avobenzone and oxybenzone), Phenylbenzimidazole sulfonic acid (Ensulizole), Benzophenone-8, and mixtures thereof.

Other exemplary sunscreens useful in the present invention (with maximum suitable amounts of each sunscreen in % wt/wt) include, but are not limited to, amino benzoic acid (about 15%), Avobenzone (about 3%), the Cinnamates, such as but not limited to cinoxate (about 3%), and octyl methoxycinnamate (Octinoxate) (about 10%), the Salicylates, such as but not limited to homosalate (about 15%), meradimate (about 5%), octocrylene (about 10%), ethylhexyl salicylate (also known as octyl salicylate or octisalate) (about 5%), oxybenzone (about 6%), dioxybenzone (about 3%), Octyldimethyl PABA (Padimate O) (about 8%), p-amyldimethyl PABA (Padimate A) (about 3%), Phenylbenzimidazole sulfonic acid (ensulizole)(about 4%), sulisobenzene (about 10%), trolamine salicylate (about 12%), benzophenone (about 10%), benzylidine compounds, such as 4-methylbenzylidine camphor (Parsol 5000) (about 6%), butyl methoxydibenzoylmethane (about 5%), bis-ethylhexyloxyphenol methoxyphenyl triazine (Bemotrizinol or Tinosorb S) (about 10%), camphor benzalkonium methosulfate (about 6%), diethyl amino hydroxy benzoyl hexyl benzoate (Uvinul A plus) (about 10%), diethylhexyl butamido triazine (Uvasorb HEB) (about 10%), disodium phenyl dibenzylmidazole tetrasulfonate (Bisdisulizole disodium or NeoHeliopan AP) (about 10%), drometrizole trisiloxane (silatriazole or Mexoryl XL) (about 15%), ethylhexyl dimethyl para-amino benzoic acid (about 8%), ethylhexyl methoxycinnamate (about 10%), ethylhexyl Triazone (Uvinul T 150) (about 5%), isoamyl p-methoxycinnamate (about 10%), 4-methylbenzylidene camphor (about 10%), methylene bis-benzotriazolyl tetramethylbutylphenol (Bisoctrizole or Tinosorb M) (about 10%), PEG-25 paramainobenzoic acid (about 5%), phenylbenziamido methylbenzylidene camphor (about 6%), diisopropyl methyl cinnamate (about 10%), dimethoxyphenyl-[1-(3,4)-4,4-dimethyl]1,3 pentanedione (about 7%), ethylhexyl dimethyloxy benzylidene dioxoimidazoline propionate (about 3%), ferulic acid (about 10%), glyceryl ethylhexanoate dimethoxycinnamate (about 10%), glycerol para-aminobenzoic acid (about 10%), phenylbenzimidazole sulfonic acid (about 3%) and Parsol SLX (benzylidene malonate polysiloxane), and mixtures thereof. The amounts listed in the preceding list are for each sunscreen individually. In some embodiments in which a combination or mixture of sunscreens is used, the total combined amount of a sunscreen may be less or equal to the sum of the maximum suitable amounts for each individual sunscreen.

As used herein, the term "Cinnamates", include but are not limited to octinoxate, cinoxate, and isoamyl p-methoxy cinnamate, and glyceryl ethylhexanoate dimethoxycinnamate.

As used herein, the term "Salicylates" include but are not limited to octisalate, homosalate, and trolamine salicylate.

As used herein, the term "Benzophenones" includes oxybenzone, sulisobenzone, and dioxybenzone.

As used herein, the term "PABA and derivatives" includes PABA (p-aminobenzoic acid), Octyldimethyl PABA (Padimate O), p-amyldimethyl PABA (Padimate A), Ethyl 4[bis (hydroxypropyl)] aminobenzoate, and glyceryl PABA.

Avobenzone, and benzophenones, as well as some other sunscreens, are photo unstable. Therefore these sunscreens are frequently combined with other sunscreens or stabilizers to increase the photostability of the final product. Some suitable photo stabilizers also referred to herein as boosters, include, but are not limited to Octocrylene, Diethylhexyl 2,6-naphthalate, and Diethylhexyl syringylidene malonate. In one embodiment, the photostabilizer is Diethylhexyl syringylidene malonate.

Although a single sunscreen may be used in a composition, typically a combination of sunscreens will be used as each sunscreen has a characteristic wavelength range in which it absorbs UV radiation (UVR) and typically that range is less than the entire range for which protection is desired. Thus, use of a combination of sunscreens provides protection over a wider range of wavelengths. Additionally, efficacy of protection is also related to the amount of sunscreen. As regulatory agencies limit the amount of each sunscreen that can be used, the use of multiple sunscreens improves the SPF while maintaining regulatory compliance.

Organic sunscreens and their efficacious wavelength range (along with suitable amounts) are as follows: amino benzoic acid (260 nm-313 nm, about 5% to about 15%); padimate 0 (290 nm-315 nm, about 1.4% to about 8%); dioxybenzone (260 nm-380 nm, about 1% to about 3%); oxybenzone (270 nm-350 nm, about 2% to about 6%); sulisobenzone (260 nm-375 nm, about 5% to about 10%); cinoxate (270 nm-328 nm, about 1% to about 3%); octocrylene (250 nm-360 nm, about 7% to about 10%); Avobenzone (320 nm-400 nm, about 1% to about 3%); octyl salicylate (280 nm-320 nm, about 3% to about 5%); homosalate (295 nm-315 nm, about 4% to about 15%); trolamine salicylate (260 nm-320 nm, about 5% to about 12%); octinoxate (290 nm-320 nm, about 2% to about 7.5%).

In one embodiment, at least two sunscreens are used where the first sunscreen has an efficacious wavelength range that includes about 280 nm to about 315 nm and the second sunscreen has an efficacious wavelength range that includes about 315 nm to about 400 nm. In one embodiment, the at least one UVA sunscreen is Avobenzone, and/or Diethylamino hydroxybenzoyl hexyl benzoate (Uvinul A Plus).

In an embodiment, the at least one UVB sunscreen is Ethylhexyl triazone (Uvinul T 150), Octyl methoxycinnamate (Octinoxate), and/or Octyl salicylate (Octisalate), alone or in mixtures thereof.

In an embodiment, the at least one sunscreen which is a UVA+UVB filter is Bemotrizinol (Tinosorb S), Iscotrizinol (Uvasorb HEB), Octocrylene, and Bisoctrizole (Tinosorb M), and mixtures thereof.

In one embodiment, the sunfilters include a combination of Bemotrizinol, Diethylamino hydroxybenzoyl hexyl benzoate, isoamyl p-methoxycinnamate, an optionally Tinosorb A2B.

In another embodiment, the sunfilters include a combination of Tinosorb S, Tinosorb M, and Octyl methoxycinnamate.

In another embodiment, the sunfilters include a combination of Tinosorb S, Tinosorb M, Octyl methoxycinnamate, and Uvinul A Plus.

In an embodiment, the at least one lamellar membrane structure comprises (i) a phospholipid; (ii) a fatty alcohol, and (iii) an ester of a $C_{12}$ to $C_{36}$ branched or straight chain fatty acid and a $C_{12}$ to $C_{36}$ branched or straight chain fatty alcohol.

In an embodiment, the at least one lamellar membrane structure comprises (i) a phospholipid present in an amount from about 0.5% to about 5% by weight, and (ii) a fatty alcohol present in an amount from about 2% to about 15% by weight, and wherein all percentages are based on the total weight of the composition.

In another embodiment, the at least one lamellar membrane structure comprises (i) a phospholipid present in an amount from about 0.5% to about 2.5% by weight, (ii) a fatty alcohol present in an amount from about 2% to about 10% by weight, and (iii) a fatty acid present in an amount from about 0.5% to about 2.5% by weight, and wherein all percentages are based on the total weight of the composition.

In yet another embodiment, the at least one lamellar membrane structure comprises (i) a phospholipid present in an amount from about 0.5% to about 2.5% by weight, (ii) a fatty alcohol present in an amount from about 2% to about 7.5% by weight, (iii) a fatty acid present in an amount from about 0.25% to about 2.5% by weight, and (iv) an ester of a branched fatty acid and a branched fatty alcohol present in an amount from about 0.25% to about 2.5% by weight, and wherein all percentages are based on the total weight of the composition.

In yet another embodiment, the at least one lamellar membrane structure comprises (i) a phospholipid present in an amount from about 0.5% to about 2.5% by weight, (ii) a fatty alcohol present in an amount from about 2% to about 7.5% by weight, and (iii) an ester of a branched fatty acid and a branched fatty alcohol present in an amount from about 0.25% to about 2.5% by weight, and wherein all percentages are based on the total weight of the composition.

Accordingly, in an embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising
  (i) a phospholipid present in an amount from about 0.5% to about 5% by weight, and (ii) a fatty alcohol present in an amount from about 2% to about 15% by weight; and
wherein in use the composition has a water vapor transmission rate of less than about 70 $g \cdot m^2 \cdot hr^{-1}$ measured in vitro using the modWVTR test methodology, and wherein all percentages are based on the total weight of the composition.

In one embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising
  (i) a phospholipid present in an amount from about 0.5% to about 2.5% by weight, (ii) a fatty alcohol present in an amount from about 2% to about 10% by weight, and (iii) a fatty acid present in an amount from about 0.5% to about 2.5% by weight; and
wherein in use the composition has a water vapor transmission rate of less than about 70 $g \cdot m^2 \cdot hr^{-1}$ measured in vitro using the modWVTR test methodology, and wherein all percentages are based on the total weight of the composition.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising
  (i) a phospholipid present in an amount from about 0.5% to about 2.5% by weight, (ii) a fatty alcohol present in an amount from about 2% to about 7.5% by weight, (iii) a fatty acid present in an amount from about 0.25% to about 2.5% by weight, and (iv) an ester of a branched fatty acid and a branched fatty alcohol present in an amount from about 0.25% to about 2.5% by weight; and
wherein in use the composition has a water vapor transmission rate of less than about 70 $g \cdot m^2 \cdot hr'$ measured in vitro using the modWVTR test methodology, and wherein all percentages are based on the total weight of the composition.

In another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising
  (i) a phospholipid present in an amount from about 0.5% to about 2.5% by weight, (ii) a fatty alcohol present in an amount from about 2% to about 7.5% by weight, and (iii) an ester of a branched fatty acid and a branched fatty alcohol present in an amount from about 0.25% to about 2.5% by weight; and wherein in use the composition has a water vapor transmission rate of less than about 70 g·m$^{-2}$·hr$^{-1}$ measured in vitro using the modWVTR test methodology, and wherein all percentages are based on the total weight of the composition.

In yet another embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid which is hydrogenated phosphatidylcholine, (ii) behenyl alcohol, (iii) behenic acid, and (iv) isostearyl isostearate; and wherein in use the composition has a water vapor transmission rate of less than about 70 g·m$^{-2}$·hr$^{-1}$ measured in vitro using the modWVTR test methodology.

In a further embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) hydrogenated phosphatidylcholine, and (ii) a mixture of behenyl alcohol and cetyl alcohol, (iii) behenic acid, and (iv) isostearyl isostearate; and wherein in use the composition has a water vapor transmission rate of less than about 70 g·m$^2$·hr$^{-1}$ measured in vitro using the modWVTR test methodology.

In one embodiment, the invention provides a topical oil-in-water emulsion composition comprising:
(a) a discontinuous oil phase;
(b) a continuous aqueous phase comprising water;
(c) a thickening agent;
(d) at least one lamellar membrane structure comprising (i) hydrogenated phosphatidylcholine present in an amount from about 0.5% to about 2.5% by weight, (ii) a fatty alcohol present in an amount from about 2% to about 7.5% by weight, which is a mixture of cetyl alcohol and behenyl alcohol, (iii) a fatty acid present in an amount from about 0.25% to about 2.5% by weight, which is behenic acid, and (iv) an ester of branched fatty acid and a branched fatty alcohol present in an amount from about 0.25% to about 2.5% by weight, which is isostearyl isostearate; and wherein in use the composition has a water vapor transmission rate of less than about 70 g·m$^{-2}$·hr$^{-1}$ measured in vitro using the modWVTR test methodology, and wherein all percentages are based on the total weight of the composition.

In an embodiment, the at least one lamellar membrane structure comprises (i) a phospholipid and (ii) a straight chain $C_{12}$-$C_{36}$ fatty alcohol.

In an embodiment, the at least one lamellar membrane structure comprises (i) a phospholipid, (ii) a straight or branched chain $C_{12}$-$C_{36}$ fatty alcohol, and (iii) a second straight or branched chain $C_{12}$-$C_{36}$ fatty alcohol.

In another embodiment, the at least one lamellar membrane structure comprises (i) a phospholipid, (ii) at least one straight or branched chain $C_{12}$-$C_{36}$ fatty alcohol, and (iii) a straight chain $C_{12}$-$C_{36}$ fatty acid.

In yet another embodiment, the at least one lamellar membrane structure comprises (i) a phospholipid, (ii) a straight or branched chain $C_{12}$-$C_{36}$ fatty alcohol, (iii) a straight or branched chain $C_{12}$-$C_{36}$ fatty acid, and (iv) an ester of a $C_{12}$ to $C_{30}$ straight or branched fatty acid and $C_{12}$ to $C_{30}$ straight or branched fatty alcohol.

In yet another embodiment, the at least one lamellar membrane structure comprises (i) a phospholipid, (ii) a straight or branched chain $C_{12}$-$C_{36}$ fatty alcohol, and (iii) a second straight or branched chain $C_{12}$-$C_{36}$ fatty alcohol, and (iii) an ester of a $C_{12}$ to $C_{30}$ straight or branched fatty acid and Cu to $C_{30}$ straight or branched fatty alcohol.

In all of the above embodiments, the composition may further comprise at least one dermatologically acceptable excipient selected from an antioxidant, a chelating agent, a preservative, a colorant, a sensate, a moisturizer, a humectant, a pH adjusting agent, a pharmaceutically acceptable agent, and combinations and mixtures thereof.

Methods of Treatment

Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, and (iii) a fatty acid; and wherein in use the composition has a water vapor transmission rate of less than about 70 g·m$^{-2}$·hr$^{-1}$ measured in vitro using the modWVTR test methodology. In one embodiment, the composition further comprises an ester of a fatty alcohol and a fatty acid.

A further embodiment of the disclosure is a method for forming an occlusive layer on the skin, the method comprising applying to the skin of a mammal in need thereof an effective amount of a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol, and (iii) a fatty acid; and wherein in use the composition has a water vapor transmission rate of less than about 70 g·m$^{-2}$·hr$^{-1}$ measured in vitro using the modWVTR test methodology. In one embodiment, the composition further comprises an ester of a fatty alcohol and a fatty acid Another embodiment of the disclosure is a method for moisturizing, and protecting, repairing, or restoring the skin lipid barrier of a mammal, the method comprising applying to the skin of the mammal in need thereof an effective amount of a topical oil-in-water emulsion composition comprising:
(a) a discontinuous oil phase;
(b) a continuous aqueous phase comprising water;
(c) a thickening agent;
(d) at least one lamellar membrane structure comprising (i) a phospholipid, (ii) a fatty alcohol and (iii) a second fatty alcohol; and wherein in use the composition has a water vapor transmission rate of less than about 70 g·m$^2$·hr' measured in vitro using the modWVTR test methodology. In one embodiment, the composition further comprises an ester of a fatty alcohol and a fatty acid The protection and repair of the skin lipid barrier by the compositions of the present invention improves the skin barrier function and conveys numerous additional therapeutic effects to a mammal to which the compositions are applied.

In one embodiment of the disclosure, the compositions described herein provide moisturization to the skin.

The compositions of the invention are applied to the skin at a frequency consistent with the condition of the skin. For example, where the skin is irritated and in need of repair, more frequent application may be required. Alternatively, where the skin is not irritated and the composition is being applied to merely protect the barrier function of the skin, less frequent application may be possible.

It should be noted that the present formulations do not include as a necessary excipient a traditional surfactant. Thus in one embodiment, the formulations of the present invention can include small amounts, e.g., 0.5%, less than 0.4%, less than 0.3%, less than 0.2%, less than 0.1% w/w, and no 0.0% w/w of a traditional surfactant. As such this is meant an anionic, cationic, non-ionic and zwiterionic surfactant.

Traditional anionic surfactants include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), docusate (dioctyl sodium sulfosuccinate), perfluorooctanesulfonate (PFOS), alkyl-aryl ether phosphates and alkyl ether phosphates. Traditional cationic surfactants include cetrimonium bromide (CTAB), cetylpyridinium chloride (CPC), and benzalkonium chloride (BAC). Traditional zwiterionic surfactants include cocamidopropyl hydroxysultaine, and cocamidopropyl betaine. Traditional non-ionic surfactants include polyethylene glycol alkyl ethers (such as Brij); polypropylene glycol alkyl ethers; glucoside alkyl ethers, such as decyl glucoside, lauryl glucoside, and octyl glucoside; polyethylene glycol octylphenyl ethers, such as Triton X-100; polyethylene glycol alkylphenyl ethers, such as Nonoxynol-9; Glycerol alkyl esters, such as glyceryl laurate; polyoxyethylene glycol sorbitan alkyl esters, such as the polysorbates; the sorbitan alkyl esters, such as the spams; and the block copolymers of polyethylene glycol and polypropylene glycol, e.g. the poloxamers.

Definitions

As used herein the term "long chain" or "fatty" such as used in reference to "fatty alcohol" or "fatty acid", etc. refers to a hydrocarbon backbone chain which may be straight or branched, saturated or unsaturated, and is suitably composed of 12 to 36 carbon atoms. In one embodiment, the chain is 16 to 26 carbon atoms. In another embodiment the chain is 16 to 22 carbon atoms. In one embodiment, the chain is 22 to 30 carbon atoms. In one embodiment, the chain is 16 to 26 carbon atoms. In another embodiment the chain is 16 to 22 carbon atoms. In another embodiment, the chain is 20 to 22 carbon atoms. In another embodiment, the chain is from 20 to 30 carbon atoms, suitably 22 to 30 carbon atoms. In another embodiment the chain is from 22 to 28 carbon atoms.

The term "applying" as used herein refers to any method which, in sound medical or cosmetic practice, delivers the topical composition to the skin of a subject in such a manner so as to provide a positive effect on a dermatological disorder, condition, or appearance.

As used herein, the phrase an "effective amount" or a "therapeutically effective amount" refers to an amount of a composition or component thereof sufficient enough to have a positive effect on the area of application. Accordingly, these amounts are sufficient to modify the skin disorder, condition, or appearance to be treated but low enough to avoid serious side effects, within the scope of sound medical advice. An effective amount will cause a substantial relief of symptoms when applied repeatedly over time. Effective amounts will vary with the particular condition or conditions being treated, the severity of the condition, the duration of the treatment, and the specific components of the composition being used.

An "effective amount" of a sunscreen is an amount of sunscreen sufficient to provide measurable protection from solar radiation as determined by having a measurable Sun Protection Factor (SPF) value and/or UVA protection value.

The term "SPF" (Sun Protection Factor) means the UVB energy required to produce a minimal erythema dose on sunscreen treated skin divided by the UVB energy required to produce a minimal erythema dose on unprotected skin.

The term "about" means within an acceptable range for the particular parameter specified as determined by one of ordinary skill in the art, which will depend, in part, on how the value is measured or determined, i.e. the limitations of the measurement system. For example, "about" can mean a range of up to 10% of a given value.

As used herein, the phrase "salts thereof" refers to salts that are pharmaceutically acceptable. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion, or an aluminium ion; or (ii) protonates an organic base such as, for example, ethanolamine, diethanolamine, triethanolamine, tromethamine and N-methylglucamine.

"%" as used herein, refers to the percentage by weight. All percentages are based on the percent by weight of the final composition prepared unless otherwise indicated and all totals equal 100% by weight.

The term "wt/wt" or "by weight", unless otherwise indicated, means the weight of a given component or specified combination of components to the total weight of the composition expressed as a percentage.

As used herein, moles, is a measure of the amount of a chemical species based upon its molecular weight. No. of moles=Mass/Molar Mass.

Mole % (mol %) is simply the number of moles of a given lamellar forming component used in a formulation relative to the total number of moles of all stated lamellar forming species, expressed as a percentage.

As used herein, the term "sensitive skin" refers to the degree of skin irritation or skin inflammation, as exemplified by parameters in suitable assays for measuring sensitivity, inflammation or irritation.

As used herein, the term "phytosterol" refers to plant sterols and plant stanols. Plant sterols are naturally occurring cholesterol-like molecules found in plants, with the highest concentrations occurring in vegetable oils. Plant stanols are hydrogenation compounds of the respective plant sterols. Phytosterols are natural components of common vegetable oils.

It should be understood that the terms "a" and "an" as used herein refer to "one or more" or "at least one" of the enumerated components. It will be clear to one of ordinary skill in the art that the use of the singular includes the plural unless specifically stated otherwise.

The term "and/or" as used herein covers both additively and also alternatively the individual elements of a list which are thus linked so that these elements are to be understood as linked selectively with "and" or respectively with "or". Furthermore, the terms used in the singular of course also comprise the plural.

Throughout the application, descriptions of various embodiments use "comprising" language, however in some specific instances, an embodiment can be described using the language "consisting essentially of" or "consisting of".

"Substantially free" of a specified component refers to a composition with less than about 1% by weight of the specified component. "Free" of a specified component refers to a composition where the specified component is absent.

As used herein, the term "sensitive skin" refers to the degree of skin irritation or skin inflammation, as exemplified by parameters in suitable assays for measuring sensitivity, inflammation or irritation.

As used herein, "mammal" includes, but is not limited to, humans, including pediatric, adult and geriatric patients.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

A designation that a substance is a semisolid, should be taken to mean the physical state of the substance in the temperature range of about 20° C. to about 40° C.

The term "organic sunscreen" means a compound or mixture of compounds that can protect human skin from UVA and/or UVB radiation and is the class of compounds classified by those skilled in the art of chemistry as organic chemicals.

The term "inorganic sunscreen" means a compound or mixture of compounds that can protect human skin from UVA and/or UVB radiation and is the class of compounds classified by those skilled in the art of chemistry as inorganic chemicals. Exemplary inorganic sunscreens include, but are not limited to, zinc oxide and titanium dioxide.

The following examples are illustrative of the present invention and are not intended to be limitations thereon.

Other terms used herein are meant to be defined by their well-known meanings in the art.

EXAMPLES

Example 1—Preparation and Characterization of Compositions Containing Phosphatidylcholine in Combination with Other Components Formulations 1-13 shown in Tables 2-4 were prepared based on the following cream composition shown in Table 1. This formulation is a representative starting point for the various changes made in Tables 2-4. This formulation is only a comparative formulation and not one covered by the present invention.

TABLE 1

| Ingredients | % |
|---|---|
| Caprylic/capric triglyceride | 5.00 |
| Diacaprylyl carbonate | 2.50 |
| Polyacrylate crosspolymer-6 | 0.50 |
| Hydroxyethyl acrylate/sodium acryloyldimethyl taurate copolymer | 0.20 |
| Glycerin | 10.00 |
| Hydroxyacetophenone | 0.50 |
| Pentylene glycol | 5.00 |
| Sodium hyaluronate | 0.10 |
| Niacinamide | 3.00 |
| D-Panthenol | 1.40 |
| Trisodium ethylenediamine disuccinate | 0.10 |
| Water | 71.70 |
| | 100.00 |

TABLE 2

| Ingredients | 1 | 2 | 3 | 4 | 5 |
|---|---|---|---|---|---|
| Caprylic/capric triglyceride | | | | | |
| Diacaprylyl carbonate | 2.50 | 2.50 | 2.50 | 2.50 | 2.50 |
| Cetyl alcohol | | | 2.03 | 3.62 | 1.67 |
| Phosphatidylcholine | 2.86 | 1.14 | 1.69 | 3.01 | 1.40 |
| Isostearyl isostearate | 5.94 | 2.17 | | | |
| Behenic acid | | | | 2.17 | 1.00 |
| Behenyl alcohol | | 5.49 | 5.08 | | 4.73 |
| Water | 67.90 | 67.90 | 67.90 | 67.90 | 67.90 |
| Glycerin | 10.00 | 10.00 | 10.00 | 10.00 | 10.00 |
| Hydroxyacetophenone | 0.50 | 0.50 | 0.50 | 0.50 | 0.50 |
| Pentylene glycol | 5.00 | 5.00 | 5.00 | 5.00 | 5.00 |
| Sodium hyaluronate | 0.10 | 0.10 | 0.10 | 0.10 | 0.10 |
| Niacinamide | 3.00 | 3.00 | 3.00 | 3.00 | 3.00 |
| D-Panthenol | 1.40 | 1.40 | 1.40 | 1.40 | 1.40 |
| Trisodium ethylenediamine disuccinate | 0.10 | 0.10 | 0.10 | 0.10 | 0.10 |
| Polyacrylate crosspolymer-6 | 0.50 | 0.50 | 0.50 | 0.50 | 0.50 |
| Hydroxyethyl acrylate/sodium acryloyldimethyl taurate copolymer | 0.20 | 0.20 | 0.20 | 0.20 | 0.20 |
| | 100.0 | 100.0 | 100.0 | 100.0 | 100.0 |
| Observed WVTR ($g \cdot m^{-2} \cdot hr^{-1}$) | 91.29 | 85.60 | 65.66 | 67.58 | 62.55 |

TABLE 3

| Ingredients | 6 | 7 | 8 | 9 | 10 |
|---|---|---|---|---|---|
| Caprylic/capric triglyceride | | | | | |
| Diacaprylyl carbonate | 2.50 | 2.50 | 2.50 | 2.50 | 2.50 |
| Cetyl alcohol | | | | 1.50 | 1.67 |
| Phosphatidylcholine | 1.40 | 1.01 | 1.40 | 1.25 | 1.39 |
| Isostearyl isostearate | 0.90 | 5.03 | | 0.90 | |
| Behenic acid | 0.90 | 2.77 | 0.90 | 0.90 | 1.00 |
| Glyceryl monobehenate | | | | 4.25 | |
| Behenyl alcohol | | | | | 4.73 |
| Water | 73.40 | 67.90 | 74.40 | 67.90 | 67.91 |
| Glycerin | 10.00 | 10.00 | 10.00 | 10.00 | 10.00 |
| Hydroxyacetophenone | 0.50 | 0.50 | 0.50 | 0.50 | 0.50 |
| Pentylene glycol | 5.00 | 5.00 | 5.00 | 5.00 | 5.00 |
| Sodium hyaluronate | 0.10 | 0.10 | 0.10 | 0.10 | 0.10 |
| Niacinamide | 3.00 | 3.00 | 3.00 | 3.00 | 3.00 |
| D-Panthenol | 1.40 | 1.40 | 1.40 | 1.40 | 1.40 |
| Trisodium ethylenediamine disuccinate | 0.10 | 0.10 | 0.10 | 0.10 | 0.10 |
| Polyacrylate crosspolymer-6 | 0.50 | 0.50 | 0.50 | 0.50 | 0.50 |
| Hydroxyethyl acrylate/sodium acryloyldimethyl taurate copolymer | 0.20 | 0.20 | 0.20 | 0.20 | 0.20 |
| | 100.0 | 100.0 | 100.0 | 100.0 | 100.0 |
| Observed WVTR (g·m$^{-2}$·hr$^{-1}$) | 88.90 | 94.30 | 100.46 | 67.32 | 55.80 |

TABLE 4

| Ingredients | 11 | 12 | 13 |
|---|---|---|---|
| Caprylic/capric triglyceride | | | |
| Diacaprylyl carbonate | | 2.50 | 2.50 |
| Cetyl alcohol | 1.67 | | |
| Phosphatidylcholine | 1.39 | 1.51 | 1.72 |
| Isostearyl isostearate | 1.00 | 1.08 | |
| Behenic acid | | 1.08 | 1.24 |
| Behenyl alcohol | 4.73 | 5.12 | 5.84 |
| Water | 67.90 | 67.90 | 67.90 |
| Glycerin | 10.00 | 10.00 | 10.00 |
| Hydroxyacetophenone | 0.50 | 0.50 | 0.50 |
| Pentylene glycol | 5.00 | 5.00 | 5.00 |
| Sodium hyaluronate | 0.10 | 0.10 | 0.10 |
| Niacinamide | 3.00 | 3.00 | 3.00 |
| D-Panthenol | 1.40 | 1.40 | 1.40 |
| Trisodium ethylenediamine disuccinate | 0.10 | 0.10 | 0.10 |
| Polyacrylate crosspolymer-6 | 0.50 | 0.50 | 0.50 |
| Hydroxyethyl acrylate/sodium acryloyldimethyl taurate copolymer | 0.20 | 0.20 | 0.20 |
| | 100.00 | 100.00 | 100.00 |
| Observed WVTR (g·m$^{-2}$·hr$^{-1}$) | 89.68 | 43.58 | 55.51 |

It should be noted that Formulations 1, 2, 6, 7, 8 and 11 shown in Table 2-4 while novel, do not meet the threshold water vapor transmission rate of less than about 70 g·m$^{-2}$·hr$^{-1}$ measured in vitro using the modWVTR test methodology as described herein.

Calculation of Mol % for Formulations 1-13

The number of moles of each component of the at least one lamellar membrane structure was calculated using the formula:

Moles=mass/molar mass (molecular weight)

Once the number of moles is known for each component of the at least one lamellar membrane structure, this can be expressed as the Mol %, as follows:

Mol %=number of moles of component X/total number of moles of components of lamellar membrane structure The number of moles or Mol % of two of more components may also be expressed as a ratio.

Formulations 1-4

TABLE 5

| | | Mass | | | |
|---|---|---|---|---|---|
| Lamellar Ingredients | Mol Wt | 1 | 2 | 3 | 4 |
| Cetyl alcohol | 242.441 | | | 2.03 | 3.62 |
| Phosphatidylcholine | 790.15 | 2.86 | 1.14 | 1.69 | 3.01 |
| Isostearyl isostearate | 536.96 | 5.94 | 2.17 | | |
| Behenic acid | 369.3099 | | | | 2.17 |
| Behenyl alcohol | 322.6 | | 5.49 | 5.08 | |

TABLE 6

| | | Moles | | | |
|---|---|---|---|---|---|
| Ingredients | Mol Wt | 1 | 2 | 3 | 4 |
| Cetyl alcohol | 242.441 | 0 | 0 | 0.008373171 | 0.014931468 |
| Phosphatidylcholine | 790.15 | 0.003619566 | 0.001442764 | 0.002138834 | 0.003809403 |
| Isostearyl isostearate | 536.96 | 0.011062277 | 0.004041269 | 0 | 0 |
| Behenic acid | 369.3099 | 0 | 0 | 0 | 0.005875824 |
| Behenyl alcohol | 322.6 | 0 | 0.017017979 | 0.015747055 | 0 |
| Total Moles | | 0.014681842 | 0.022502012 | 0.026259061 | 0.024616695 |

TABLE 7

| | | Mol % | | | |
|---|---|---|---|---|---|
| Mol % | Mol Wt | 1 | 2 | 3 | 4 |
| Cetyl alcohol | 242.441 | 0 | 0 | 31.88678862 | 60.65585869 |
| Phosphatidylcholine | 790.15 | 24.65334936 | 6.411711146 | 8.145129091 | 15.47487689 |

TABLE 7-continued

| Mol % | Mol Wt | Mol % 1 | 2 | 3 | 4 |
|---|---|---|---|---|---|
| Isostearyl isostearate | 536.96 | 75.34665064 | 17.95959095 | 0 | 0 |
| Behenic acid | 369.3099 | 0 | 0 | 0 | 23.86926442 |
| Behenyl alcohol | 322.6 | 0 | 75.6286979 | 59.96808229 | 0 |
| | | 100 | 100 | 100 | 100 |

Formulations 5-8

TABLE 8

| Lamellar Ingredients | Mol Wt | Mass 5 | 6 | 7 | 8 |
|---|---|---|---|---|---|
| Cetyl alcohol | 242.441 | 1.67 | | | |
| Phosphatidylcholine | 790.15 | 1.4 | 1.4 | 1.01 | 1.4 |
| Isostearyl isostearate | 536.96 | | 0.9 | 5.03 | |
| Behenic acid | 369.3099 | 1 | 0.9 | 2.77 | 0.9 |
| Behenyl alcohol | 322.6 | 4.73 | | | |

TABLE 9

| Ingredients | Mol Wt | Moles 5 | 6 | 7 | 8 |
|---|---|---|---|---|---|
| Cetyl alcohol | 242.441 | 0.006888274 | 0 | 0 | 0 |
| Phosphatidylcholine | 790.15 | 0.001771815 | 0.001771815 | 0.001278238 | 0.001771815 |
| Isostearyl isostearate | 536.96 | 0 | 0.001676103 | 0.009367551 | 0 |
| Behenic acid | 369.3099 | 0.002707753 | 0.002436978 | 0.007500476 | 0.002436978 |
| Behenyl alcohol | 322.6 | 0.01466212 | 0 | 0 | 0 |
| Total Moles | | 0.026029963 | 0.005884896 | 0.018146265 | 0.004208793 |

TABLE 10

| Mol % | Mol Wt | Mol % 5 | 6 | 7 | 8 |
|---|---|---|---|---|---|
| Cetyl alcohol | 242.441 | 26.46286492 | 0 | 0 | 0 |
| Phosphatidylcholine | 790.15 | 6.806830665 | 30.10784841 | 7.044084938 | 42.09794572 |
| Isostearyl isostearate | 536.96 | 0 | 28.48143088 | 51.6224729 | 0 |
| Behenic acid | 369.3099 | 10.40244685 | 41.41072071 | 41.33344216 | 57.90205428 |
| Behenyl alcohol | 322.6 | 56.32785757 | 0 | 0 | 0 |
| | | 100 | 100 | 100 | 100 |

Formulations 9-12

TABLE 11

| Lamellar Ingredients | Mol Wt | Mass 9 | 10 | 11 | 12 |
|---|---|---|---|---|---|
| Cetyl alcohol | 242.441 | 1.5 | 1.67 | 1.67 | |
| Phosphatidylcholine | 790.15 | 1.25 | 1.39 | 1.39 | 1.51 |
| Isostearyl isostearate | 536.96 | 0.9 | | 1 | 1.08 |
| Behenic acid | 369.3099 | 0.9 | 1 | | 1.08 |
| Behenyl alcohol | 322.6 | | 4.73 | 4.73 | 5.12 |
| Glyceryl Monobehenate | 414.662 | 4.25 | | | |

TABLE 12

| Ingredients | Mol Wt | Moles | | | |
|---|---|---|---|---|---|
| | | 9 | 10 | 11 | 12 |
| Cetyl alcohol | 242.441 | 0.006187072 | 0.006888274 | 0.006888274 | 0 |
| Phosphatidylcholine | 790.15 | 0.001581978 | 0.00175916 | 0.00175916 | 0.00191103 |
| Isostearyl isostearate | 536.96 | 0.001676103 | 0 | 0.001862336 | 0.002011323 |
| Behenic acid | 369.3099 | 0.002436978 | 0.002707753 | 0 | 0.002924373 |
| Behenyl alcohol | 322.6 | 0 | 0.01466212 | 0.01466212 | 0.015871048 |
| Glyceryl Monobehenate | 414.662 | 0.010249311 | 0 | 0 | 0 |
| Total Moles | | 0.022131442 | 0.026017307 | 0.02517189 | 0.022717774 |

TABLE 13

| Mol %'s | Mol Wt | Mol % | | | |
|---|---|---|---|---|---|
| | | 9 | 10 | 11 | 12 |
| Cetyl alcohol | 242.441 | 27.95602871 | 26.47573748 | 27.3649451 | 0 |
| Phosphatidylcholine | 790.15 | 7.148102213 | 6.761497901 | 6.988587909 | 8.412045952 |
| Isostearyl isostearate | 536.96 | 7.573399385 | 0 | 7.398475532 | 8.853521662 |
| Behenic acid | 369.3099 | 11.0113824 | 10.40750701 | 0 | 12.87262267 |
| Behenyl alcohol | 322.6 | 0 | 56.35525761 | 58.24799146 | 69.86180971 |
| Glyceryl Monobehenate | 414.662 | 46.31108729 | 0 | 0 | 0 |
| | | 100 | 100 | 100 | 100 |

Formulation 13

TABLE 14

| Lamellar Ingredients | Mol Wt | Mass |
|---|---|---|
| | | 13 |
| Cetyl alcohol | 242.441 | |
| Phosphatidylcholine | 790.15 | 1.72 |
| Isostearyl isostearate | 536.96 | |
| Behenic acid | 369.3099 | 1.24 |
| Behenyl alcohol | 322.6 | 5.84 |
| Glyceryl Monobehenate | 414.662 | |

TABLE 15

| Ingredients | Mol Wt | Moles |
|---|---|---|
| | | 13 |
| Cetyl alcohol | 242.441 | 0 |
| Phosphatidylcholine | 790.15 | 0.002176802 |
| Isostearyl isostearate | 536.96 | 0 |
| Behenic acid | 369.3099 | 0.003357614 |
| Behenyl alcohol | 322.6 | 0.018102914 |
| Glyceryl Monobehenate | 414.662 | 0 |
| Total Moles | | 0.023637329 |

TABLE 16

| Mol % | Mol Wt | Mol % |
|---|---|---|
| | | 13 |
| Cetyl alcohol | 242.441 | 0 |
| Phosphatidylcholine | 790.15 | 9.209170086 |
| Isostearyl isostearate | 536.96 | 0 |
| Behenic acid | 369.3099 | 14.20470854 |
| Behenyl alcohol | 322.6 | 76.58612138 |
| Glyceryl Monobehenate | 414.662 | 0 |
| | | 100 |

Method of Preparation

Formulations 1-13 were prepared using a simple "single pot" process, as follows:

1. Add all components (except polymer) to a reaction vessel and heat to 85° C. (+/−3° C.).
2. Add polymer and homogenize at 12,000 rpm until a temperature of 60° C. is reached.
3. Place reaction vessel in a water bath of freshly drawn water. Homogenize and cool composition to a temperature of 40° C.
4. Adjust pH to 5.5 (+/−0.3).
5. Added water to compensate for evaporative losses.
6. Re-homogenize for 2 minutes.

Measurement of Water Vapor Transmission Rate

The ability of the compositions to form an occlusive layer on the skin was evaluated by measuring the water vapor transmission rate (WVTR). The following method, based upon Pennick et al., Intl J Cosmetic Sci, 2012, 34, p 567-574, and G. Pennick, et al., Int J Cosmet Sci, 32 (2010) 304-312; with minor changes as noted below was used. This method is referenced herein (and in the claims) as "modWVTR test methodology". This paper also describes a suitable means for testing Lamellar Thickness.

1. Vitro-Skin (IMS Inc., Portland, Me.) was cut into circular discs using a hole-punch. The discs were weighed on an analytical balance (not Vitro-Corneum as in the Pennick et al. paper.)

2. The discs were taped on opposing edges, rough side up, with adhesive tape and fixed to the glass surface of a pneumatic drive (Byko Drive). A weighted bar was placed on the drive arm and a 50 μm gauge block placed in front of the weighted bar.
3. The test cream was applied in front of the gauge block, such that when the pneumatic arm is actuated a thin film of cream is applied to the surface including the taped Vitro-Skin disc. Typically 4 discs were coated in a single pass of the arm. The button was depressed and the first coat of the disc occurred. The coated discs were left for 8-10 minutes.
4. The adhesive tape was carefully removed and the discs placed onto a mesh drying tray at room temperature. The surface of the drive unit was cleaned and then the process (steps 1-3) repeated for the next samples.
5. Once all the samples had received their initial coat of cream, the first (and most dry samples) was secured in place for a second application of cream perpendicular to the first coat. The discs were then removed and allowed to partially dry for 60 minutes. The process was repeated for the other samples.
6. The coated discs were reweighed and the weight of applied cream determined.
7. Following partial drying, the WVTR cells were filled with 190 μL of deionized water. The discs were then secured in place over the water, coated side up, using the upper portion of the WVTR cell which was screwed into place. The loaded cells were then reweighed to give the initial weight. The WVTR cells are commercially available from Payne Cells from SMS (Surface Measurement Systems, UK).
8. The WVTR cells were placed in a desiccator over silica gel desiccant. Relative humidity was typically 24-28% RH. The cells were removed periodically.
9. Weight values were determined over a 45-240 minute period. WVTR was calculated using the standard WVTR formula described by Pennick et al (Intl. J. Cosmetic Sci., vol. 34, pp 567-574, 2012). Non-normalized WVTR values were obtained.

The WVTR was calculated by the formula $$WVTR(g \cdot m^2 \cdot hr^{-1}) = \frac{\text{Water Loss}(g)(W_{0.75} - W_{3.0})}{\text{Area of Membrane }(m^2) \times \text{Time}(h)} \quad \text{Formula 1}$$

The area of the membrane was $1.22 \times 10^4$ m$^2$. $W_{0.75}$ and $W_{3.0}$ were the WVTR cell weights in grams at the 0.75 and 3 hour time points respectively.

Characterization Using X-Ray defractionS

Small angle X-ray scattering (SAXS) and wide angle X-ray scattering (WAXS) data of undried and dried creams at ambient temperature was collected with a SAXSLAB Ganesha SAXS/MAXS/WAXS system at the Shared Materials Instrumentation Facility (SMIF), Duke University, Durham, N.C. The Ganesha uses an X-ray point source. SAXS data was collected in a 2-slit mode with the sample-detector distance equal to 441 mm, a 2 mm beam stop, and aperture size=0.9-0.4 mm. WAXS data was collected in a 2-slit mode with a sample—detector distance=101 mm, a 2 mm beam stop, and an aperture size=0.9 mm. Samples were loaded into SAXSLAB "button cells" equipped with 5-7 microns thick mica windows and an approximate pathlength of 1 mm. Data was not mathematically desmeared.

Additional SAXS data was collected with an Anton Paar SAXSess mc2 system using an Anton Parr paste cell (pathlength of approximately 0.7 mm) with polycarbonate windows. The paste cell comes in two halves and one of the halves was loaded with cream. The other half was sealed with an O-ring to the filled halve. The Anton Parr system uses an X-ray line source, a semitransparent beamstop, and a 1D detector with a sample—detector distance of 306.8 mm. The resulting desmeared data was desmeared with Anton Parr software. The Ganesha data were collected at 15 seconds per frame with a 2D detector and the Anton Parr data were collected at 10 seconds per frame. The total data collection time for each run was 30 minutes. Both systems used copper K-alpha radiation.

Samples were analyzed wet and dried. Dried samples were prepared by drying approximately 1 mm thick creams in a SAXSLAB button cell for approximately 11 hours while stored in a chamber purged with nitrogen gas and by drying approximately 0.7 mm thick creams in a Anton Parr paste cell for 3 hours in the same chamber. Percent weight losses from drying were approximately 60.

The undried and dried samples prepared for the Anton Parr runs were temperature controlled to 25° C. and 32° C., respectively. The dried samples were run at 32° C. to simulate the conditions the cream would experience after applying to the skin and letting the rubbed-in cream dry.

Data was exported in PDH format and reformatted in Excel and imported into PANalytical HighScorePlus software. The data was then stripped of the copper K-alpha 2 contribution. The background was modelled, peaks located, and profile fitted (PROFIT).

Characterization Using FTIR

Each formulated cream was analyzed by transmission FTIR in triplicate by preparing a dried film on a 13×1 mm ZnSe crystal via the following protocol:

Approximately 1-3 mg of sample is deposited onto a single ZnSe crystal and then sandwiched with microscope cover slip. The cover slip is removed and the remaining cream on the ZnSe crystal is dried for 60 minutes in a desiccator ((26% RH (+/−3% RH) and 21° C. (+/−2° C.)). Following this drying period, a second ZnSe crystal is gently pressed onto the crystal with the dried cream, mounted into a Specac solids sample holder, inserted into the Specac heating jacket (Swedesboro, N.J.) assembly, and then mounted into the FTIR spectrometer.

FTIR spectra were acquired with Nicolet iS50 FTIR spectrometer (Thermo Scientific, NH, USA) equipped with Mercury-Cadmium-Telluride (MCT) detector, a Specac electrical heating jacket, a specac transmission solid cell holder, a Simplex scientific temperature controller (Middleton, Wis., USA) and a NesLab Digital Plus circulation bath. Thermotropic spectral acquisition was managed via TempProfile v2.2.3 (Simplex Scientific, Middleton, Wis.) and OMNIC v9.2.98 software. This particular version of TempProfile contained a temperature DDE output that enabled automated circulation bath control for cooling via a separate software script.

Thermotropic FTIR was conducted on each lipid system from 25° C. to 80° C. at a ramp rate of 1° C. per minute. Atmospheric suppressed absorbance spectra were collected at 1 spectrum per minute, at 4 cm$^{-1}$ resolution and 16 co-addition. Temperature for each acquired spectrum was recorded in the spectrum title via the TempProfile software. Post-acquisition, spectra were saved as individual .spc files in GRAMS software (ThermoScientific, NH, USA).

Results

The water vapor transmission rates for Formulations 1-13 are illustrated in Table 17:

TABLE 17

| Formulation number | Composition | WVTR $g \cdot m^{-2} \cdot hr^{-1}$ | Std Dev | Removal |
|---|---|---|---|---|
| 1 | PC, ISIS | 91.29 | 2.39 | COH, BOH, BCOOH |
| 2 | PC, BOH, ISIS | 85.60 | 9.24 | COH, BCOOH |
| 3 | PC, COH, BOH | 65.66 | 1.34 | BCOOH, ISIS |
| 4 | PC, COH, BCOOH | 67.58 | 13.57 | BOH, ISIS |
| 5 | PC, COH, BOH, BCOOH | 62.55 | 1.85 | ISIS |
| 6 | PC, BCOOH, ISIS (not wt corrected) | 88.90 | 1.90 | COH, BOH |
| 7 | PC, BCOOH, ISIS (wt corrected) | 94.30 | 0.20 | COH, BOH |
| 8 | PC, BCOOH | 100.46 | 3.60 | COH, BOH, ISIS |
| 9 | PC, COH, BCOOH, ISIS, fractionated GMB | 67.32 | 1.20 | BOH |
| 10 | PC, COH, BOH, BCOOH | 55.80 | 1.34 | ISIS |
| 11 | PC, COH, BOH, ISIS | 89.68 | 12.62 | BCOOH |
| 12 | PC, BOH, BCOOH, ISIS | 43.58 | 5.43 | COH |
| 13 | PC, BOH, BCOOH | 55.51 | 2.19 | COH, ISIS |

PC = Phosphatidylcholine;
ISIS = Isostearyl isostearate;
COH = Cetyl alcohol;
BOH = Behenyl alcohol;
Behenic acid = BCOOH Formulation 1 containing phosphatidylcholine and ISIS had a WVTR of 91.29 $g \cdot m^{-2} \cdot hr^{-1}$. Similarly, Formulation 8 containing phosphatidylcholine and behenic acid (i.e. no fatty alcohol) had a WVTR of 100.46 $g \cdot m^{-2} \cdot hr^{-1}$. A similar result was obtained for Formulations 6 and 7, containing phosphatidylcholine, behenic acid and ISIS (i.e. no fatty alcohol).

By contrast, Formulation 3 which contained phosphatidylcholine, cetyl alcohol and behenyl alcohol had a WVTR of 65.66 $g \cdot m^{-2} \cdot hr^{-1}$. This indicated that improved occlusion may be obtained from a composition containing phosphatidylcholine and fatty alcohol. Note however that compositions containing phosphatidylcholine, fatty alcohol and ISIS performed poorly—see Formulations 2 and 11 which had a WVTR of 85.60 and 89.68 $g \cdot m^{-2} \cdot hr^{-1}$, respectively.

The addition of behenic acid to Formulation 3 resulted in a further improvement in the WVTR. See Formulations 5 and 10 which had a WVTR of 62.55 $g \cdot m^{-2} \cdot hr^{-1}$ and 55.80 $g \cdot m^{-2} \cdot hr^{-1}$, respectively. This indicated that a composition containing a combination of phosphatidylcholine, fatty alcohol and fatty acid is desirable for its ability to form an occlusive layer on the skin.

A composition containing a mixture of phosphatidylcholine, behenyl alcohol, behenic acid and isostearyl isostearate resulted in further improvement. See Formulation 12 which had a WVTR of 43.58 $g \cdot m^{-2} \cdot hr^{-1}$.

Taken together, the data illustrates that a preparation containing phosphatidylcholine and fatty alcohol offers improved levels of occlusion (see Formulation 3). However, the further addition of a fatty acid such as behenic acid improves the level of occlusion (see Formulation 5 and 10). The packing structure of Formulation 10 was determined using wide-angle X-ray scattering (WAXS) and found to be orthorhombic form, consistent with the formation of a planar lipid bilayer structure.

The best level of occlusion was observed from a composition containing phosphatidylcholine, behenyl alcohol, behenic acid and isostearyl isostearate (see Formulation 12). The packing structure of Formulation 12 was also determined using WAXS and found to be orthorhombic form, consistent with the formation of a planar lipid bilayer structure.

Or put differently, the data illustrates that the presence of phosphatidylcholine and fatty alcohol is critical and that incremental improvement may be obtained from the further addition of a fatty acid, or from the further addition of a fatty acid and an ester of a branched fatty acid and a branched fatty alcohol. It is thought that longer chain (i.e. $C_{12}$-$C_{36}$ and more especially $C_{18}$-$C_{36}$) fatty alcohols and fatty acids are desirable because of their ability to pack in close proximity with the phospholipid component and initiate hydrogen bonding interactions.

Example 2—Additional Compositions

The following additional compositions were prepared and shown in Table 18 and 19 below.

TABLE 18

Formulations 14-17 (lotions)

| Ingredients | Material | 14 lotion with 1% Peptide | 15 lotion with 0.25% Pterowhite (2.5% IPD) | 16 lotion with 0.5% shea tris | 17 lotion |
|---|---|---|---|---|---|
| Water | Water | 61.200 | 59.450 | 61.700 | 62.200 |
| Lamellar Blend | Cetyl alcohol | 1.500 | 1.500 | 1.500 | 1.500 |
| | Behenic acid | 0.900 | 0.900 | 0.900 | 0.900 |
| | Behenyl alcohol | 4.250 | 4.250 | 4.250 | 4.250 |
| | Hydrogenated phosphatidylcholine | 1.250 | 1.250 | 1.250 | 1.250 |
| | ISIS | 0.900 | 0.900 | 0.900 | 0.900 |
| Strengthen Barrier (inside out) | Niacinamide | 3.000 | 3.000 | 3.000 | 3.000 |
| | Peptide | 1.000 | | | |
| Waxes/Butters | Shea butter | | | | |
| | Petrolatum | 10.000 | 10.000 | 10.000 | 10.000 |
| Polymer | Sepimax Weo | | | | |
| | Polyacrylate crosspolymer-6 | 0.500 | 0.500 | 0.500 | 0.500 |
| Humectants | Glycerin | 10.000 | 10.000 | 10.000 | 10.000 |
| | Panthenol | 1.500 | 1.500 | 1.500 | 1.500 |
| Preservative System | Pentylene glycol | 1.500 | 1.500 | 1.500 | 1.500 |
| | Hexylene glycol | 1.600 | 1.600 | 1.600 | 1.600 |
| | Trisodium ethylenediamine disuccinate | 0.200 | 0.200 | 0.200 | 0.200 |
| Additional Bioactives | PMEA | 0.700 | 0.700 | 0.700 | 0.700 |
| | Ptero white | | 0.250 | | |
| | Shea Tris | | | 0.500 | |
| Solubilizer | Isopentyldiol | | 2.500 | | |
| | | 100.000 | 100.000 | 100.000 | 100.000 |

TABLE 19

Formulations 18-21 (balms)

| Ingredients | Material | 18 balm with 1% Peptide | 19 balm with 0.25% Pterowhite | 20 balm with 0.5% shea tris | 21 balm |
|---|---|---|---|---|---|
| Water | Water | 51.200 | 51.950 | 51.700 | 52.200 |
| Lamellar Blend | Cetyl alcohol | 1.500 | 1.500 | 1.500 | 1.500 |
| | Behenic acid | 0.900 | 0.900 | 0.900 | 0.900 |
| | Behenyl alcohol | 4.250 | 4.250 | 4.250 | 4.250 |
| | Hydrogenated phosphatidylcholine | 1.250 | 1.250 | 1.250 | 1.250 |
| | ISIS | 0.900 | 0.900 | 0.900 | 0.900 |
| Strengthen Barrier (inside out) | Niacinamide | 3.000 | 3.000 | 3.000 | 3.000 |
| | Peptide | 1.000 | | | |
| Waxes/Butters | Shea butter | 5.000 | 5.000 | 5.000 | 5.000 |
| | Petrolatum | 10.000 | 10.000 | 10.000 | 10.000 |
| Polymer | Sepimax Weo | | | | |
| | Polyacrylate crosspolymer-6 | 0.500 | 0.500 | 0.500 | 0.500 |
| Humectants | Glycerin | 10.000 | 10.000 | 10.000 | 10.000 |
| | Panthenol | 1.500 | 1.500 | 1.500 | 1.500 |
| Preservative System | Pentylene glycol | 1.500 | 1.500 | 1.500 | 1.500 |
| | Hexylene glycol | 1.600 | 1.600 | 1.600 | 1.600 |
| | Trisodium ethylenediamine disuccinate | 0.200 | 0.200 | 0.200 | 0.200 |
| Additional Bioactives | PMEA | 0.700 | 0.700 | 0.700 | 0.700 |
| | Ptero white | | 0.250 | | |
| | Shea Tris | | | 0.500 | |
| Solubilizer | Isopentyldiol | 5.000 | 5.000 | 5.000 | 5.000 |
| | | 100.000 | 100.000 | 100.000 | 100.000 |

43

Calculation of Mol % for Formulations 14-21

TABLE 20

| Lamellar Ingredients | Mass | |
|---|---|---|
| | Mol Wt | Formulations 14-21 |
| Cetyl alcohol | 242.441 | 1.5 |
| Phosphatidylcholine | 790.15 | 1.25 |
| Isostearyl isostearate | 536.96 | 0.9 |
| Behenic acid | 369.3099 | 0.9 |
| Behenyl alcohol | 322.6 | 4.25 |
| Glyceryl Monobehenate | 414.662 | |
| Observed WVTR (g · m$^{-2}$ · hr$^{-1}$) | | About 40 |

TABLE 21

| Ingredients | Moles | |
|---|---|---|
| | Mol Wt | Formulations 14-21 |
| Cetyl alcohol | 242.441 | 0.006187072 |
| Phosphatidylcholine | 790.15 | 0.001581978 |
| Isostearyl isostearate | 536.96 | 0.001676103 |
| Behenic acid | 369.3099 | 0.002436978 |
| Behenyl alcohol | 322.6 | 0.01317421 |
| Glyceryl Monobehenate | 414.662 | 0 |
| | Total Moles | 0.02505634 |

TABLE 22

| Mol % | Mol % | |
|---|---|---|
| | Mol Wt | Formulations 14-21 |
| Cetyl alcohol | 242.441 | 24.69264174 |
| Phosphatidylcholine | 790.15 | 6.313683853 |
| Isostearyl isostearate | 536.96 | 6.689334873 |
| Behenic acid | 369.3099 | 9.725992327 |
| Behenyl alcohol | 322.6 | 52.57834721 |
| Glyceryl Monobehenate | 414.662 | 0 |
| | | 100 |

Method of Preparation

Formulations 14-21 were prepared using the following general method/process:
1. Add all components (except polymer, and peptide/Ptero white where applicable) to a reaction vessel and heat to 80° C., whilst mixing.
2. Add polymer.
3. Homogenize (25 m/s) for 10 minutes and cool to 40° C.
4. Add peptide and Ptero white, where applicable.
5. Homogenize (25/s) for 10 minutes.

Characterization of Additional Compositions

Formulations 14 (lotion) and 18 (balm) were characterized using the methodologies described in Example 1. The test results are shown in Table 23. In particular, the water vapor transmission rate was measured to determine the level of occlusiveness of the compositions. Also, small angle X-ray defraction (SAXS) was used to determine the thickness of the bi-layer structure and Fourier transform infrared spectroscopy (FTIR) was used to determine the level of orderedness of the alkyl groups in the components of the bilayer structure.

44

TABLE 23

| Method of characterization | Formulation 14 | Formulation 18 |
|---|---|---|
| WVTR | approximately 40 | approximately 40 |
| SAXS | 18.4 nm wet and 7.2 nm dry | 18.0 nm wet and 6.7 nm dry |
| FTIR | <2850, 45 | <2850, 45 |

Collectively, the data illustrate that the compositions of the invention are able to form an occlusive layer on the skin and have an ordered bilayer structure.

Example 3—Comparative Compositions

The following comparative compositions were prepared—see Table 24. That is, for Formulations 22 and 23, the DuraQuench IQ blend described in WO 2012/104604, and commercially available from Croda Chemicals, was added to the base formulation shown in Table 1. For Formulation 24, the ProLipid® 141 blend as described in U.S. Pat. No. 5,849,315 was added to the base formulation shown in Table 1.

TABLE 24

| Ingredients | 22 | 23 | 24 |
|---|---|---|---|
| Caprylic/capric triglyceride | 5.00 | 5.00 | 5.00 |
| Dicaprylyl carbonate | 7.50 | 7.50 | 7.50 |
| Duraquench IQ | 3.50 | 5.00 | |
| ProLipid 141 | | | 3.00 |
| Glyceryl stearate, behenyl alcohol, palmitic acid, stearic acid, lecithin, lauryl alcohol, myristyl alcohol, cetyl alcohol | | | |
| Vegetable oil | 2.00 | 2.00 | 2.00 |
| Butyrospermum parkii (Shea butter) | 1.60 | 1.60 | 1.60 |
| Polyacrylate crosspolymer-6 | 0.50 | 0.50 | 0.50 |
| Hydroxyethyl acrylate/Sodium acryloyldimethyl taurate copolymer | 0.20 | 0.20 | 0.20 |
| Sodium hyaluronate | 0.10 | 0.10 | 0.10 |
| Water | 59.60 | 58.10 | 60.10 |
| Glycerin | 10.00 | 10.00 | 10.00 |
| Hydroxyacetophenone | 0.50 | 0.50 | 0.50 |
| Pentylene glycol | 5.00 | 5.00 | 5.00 |
| Niacinamide | 3.00 | 3.00 | 3.00 |
| D-Panthenol | 1.40 | 1.40 | 1.40 |
| Trisodium ethylenediamine disuccinate | 0.10 | 0.10 | 0.10 |
| | 100.00 | 100.00 | 100.00 |
| Observed WVTR (g · m$^2$ · hr$^{-1}$) | 93.2 | 89.68 | 94.42 |

Method of Preparation
1. Heat oils; Note: Formulation 24 was heated to 85-90° C., and Formulations 22 and 23 were heated to 100° C. (i.e. because a milky white appearance was observed which did not dissipate even on heating to 100° C.).
2. Add polymer at 85° C. with gentle homogenization.
3. Add water phase (bulk of water and glycerol, plus pentylene glycol for Formulations 22 and 23) heated to 75° C.
4. Homogenize at 12,000 rpm.
5. Heat a separate phase containing sodium hyaluronate, niacinamide, panthenol, trisodium ethylenediamine disuccinate and a small portion of water (plus pentylene glycol for Formulation 24) to 40-45° C. until dissolved and cooled to 30° C.
6. Add phase from step 5 to the bulk composition at 35° C.
7. Adjust pH to 5.5 (+1-0.3).

8. Add water to compensate for evaporative losses and re-homogenize briefly to incorporate added water.

Measurement of Water Vapor Transmission Rate

The water vapor transmission rate (WVTR) of the three comparative compositions was determined using the same method described in Example 1. An additional comparative example is the Physiogel Hand Cream, noted herein as Formulation 25. The results are shown in Table 25 below:

TABLE 25

| Formulation number | Observed WVTR (g · m$^{-2}$ · hr$^{-1}$) | Std Dev |
|---|---|---|
| 22 | 93.2 | 3.88 |
| 23 | 89.68 | 3.44 |
| 24 | 94.42 | 4.2 |
| 25 | 72.02 | 3.5 |

The comparative compositions were observed to have a dramatically greater WVTR than the compositions of the present invention which have a WVTR of less than about 70 g·m$^{-2}$·hr$^{-1}$. This is consistent with the observation that the present inventive compositions have improved levels of occlusivity compared with those of the prior art.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A topical oil-in-water emulsion composition comprising:
    (a) a discontinuous oil phase;
    (b) a continuous aqueous phase comprising water;
    (c) a thickening agent;
    (d) at least one lamellar membrane structure comprising (i) a phospholipid which is hydrogenated phosphatidylcholine, (ii) a fatty alcohol which is behenyl alcohol or a mixture of cetyl alcohol and behenyl alcohol, (iii) a fatty acid which is behenic acid, and (iv) an ester of a fatty acid and a fatty alcohol which is isostearyl isostearate, wherein the fatty alcohol and the phospholipid are present in a weight ratio of from about 10:1 to about 1:1; the fatty alcohol and the fatty acid are present in a weight ratio of from about 10:1 to about 1:1; and the fatty alcohol and the ester are present in a weight ratio of from about 10:1 to about 1:1; and wherein in use the composition has a water vapor transmission rate of less than about 70 g·m$^{-2}$·hr$^{-1}$ measured in vitro using the modWVTR test methodology.

2. The composition according to claim 1 wherein the composition further comprises glycerin in an amount from about 5% to about 15% by weight, based on the total weight of the composition.

3. The composition according to claim 1 wherein the phospholipid is present in an amount from about 0.5% to about 5% by weight, based on the total weight of the composition.

4. The composition according to claim 1 wherein the fatty alcohol is present in an amount from about 2% to about 15% by weight, based on the total weight of the composition.

5. The composition according to claim 1 wherein the fatty acid is present in an amount from about 0.1% to about 5% by weight, based on the total weight of the composition.

6. The composition according to claim 1, wherein the ester is present in an amount from about 0.1% to about 5% by weight, based on the total weight of the composition.

7. The composition according to claim 1, which further comprises at least one dermatologically acceptable excipient selected from an antioxidant, a chelating agent, a preservative, a colorant, a sensate, a moisturizer, a humectant, a pH adjusting agent, and combinations and mixtures thereof.

8. The composition according to claim 1, which further comprises at least one pharmaceutically acceptable active agent.

9. A method for moisturizing, and protecting, repairing, or restoring the skin lipid barrier of a mammal, the method comprising applying to the skin of the mammal in need thereof an effective amount of the topical oil-in-water emulsion composition comprising a composition according to claim 1.

10. The composition according to claim 1 wherein the weight ratio of the phospholipid:fatty alcohol:fatty acid:ester is about 1.4:6.4:1:1.

* * * * *